US012029638B2

(12) United States Patent
La Francesca et al.

(10) Patent No.: US 12,029,638 B2
(45) Date of Patent: *Jul. 9, 2024

(54) SYSTEMS AND METHODS FOR PRODUCING GASTROINTESTINAL TISSUES

(71) Applicant: Biostage, Inc., Holliston, MA (US)

(72) Inventors: Saverio La Francesca, Houston, TX (US); Sherif Soliman, Holliston, MA (US); Matthew Marsh, Holliston, MA (US); Shunfu Hu, Holliston, MA (US); Linghui Meng, Holliston, MA (US)

(73) Assignee: HARVARD APPARATUS REGENERATIVE TECHNOLOGY, INC, Holliston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/589,096

(22) Filed: Jan. 31, 2022

(65) Prior Publication Data

US 2022/0226097 A1 Jul. 21, 2022

Related U.S. Application Data

(63) Continuation of application No. 16/391,212, filed on Apr. 22, 2019, now Pat. No. 11,234,805, which is a
(Continued)

(51) Int. Cl.
*A61F 2/04* (2013.01)
*A61F 2/00* (2006.01)
(Continued)

(52) U.S. Cl.
CPC .............. *A61F 2/04* (2013.01); *A61F 2/0077* (2013.01); *A61F 2/07* (2013.01); *A61F 2/82* (2013.01);
(Continued)

(58) Field of Classification Search
CPC ...... A61F 2/04; A61F 2/07; A61F 2/82; A61F 2/0077; A61F 2/90; A61F 2250/0067; A61F 2002/0086; A61F 2002/043; A61F 2002/044; A61F 2002/045; A61F 2002/046; A61F 2210/0076; C12M 21/08; C12M 25/14; A61L 27/04; A61L 27/18; A61L 27/3834; A61L 27/56; A61L 27/58
See application file for complete search history.

(56) References Cited

U.S. PATENT DOCUMENTS 4,043,331 A 8/1977 Martin et al.
4,889,119 A 12/1989 Jamiolkowski et al.
(Continued)

FOREIGN PATENT DOCUMENTS

RU 2402983 C2 11/2010
WO 2013116479 A1 8/2013
WO 2014004746 A2 1/2014

OTHER PUBLICATIONS

Holt-Casper D. et al., Novel xeno-free human heart matrix-derived three-dimensional scaffolds. J Transl Med., Jun. 18, 2015, 13:1944. DOI: 10.1186/s12967015-0559-0, pp. 1-15.

*Primary Examiner* — Dinah Baria
(74) *Attorney, Agent, or Firm* — Young Basile Hanlon & MacFarlane, P.C.

(57) ABSTRACT

Aspects of the disclosure relate methods and synthetic scaffolds for regenerating gastrointestinal tissue (e.g., esophageal tissue).

24 Claims, 16 Drawing Sheets

Related U.S. Application Data continuation of application No. 16/020,053, filed on Jun. 27, 2018, which is a continuation of application No. 15/350,970, filed on Nov. 14, 2016, now Pat. No. 10,265,153, said application No. 16/391,212 is a continuation of application No. 15/350,970, filed on Nov. 14, 2016, now Pat. No. 10,265,153.

(60) Provisional application No. 62/276,715, filed on Jan. 8, 2016, provisional application No. 62/254,700, filed on Nov. 12, 2015.

(51) Int. Cl.
| | | |
|---|---|---|
| *A61F 2/07* | (2013.01) | |
| *A61F 2/82* | (2013.01) | |
| *A61L 27/04* | (2006.01) | |
| *A61L 27/18* | (2006.01) | |
| *A61L 27/38* | (2006.01) | |
| *A61L 27/56* | (2006.01) | |
| *A61L 27/58* | (2006.01) | |
| *C12M 1/12* | (2006.01) | |
| *C12M 3/00* | (2006.01) | |
| *A61F 2/90* | (2013.01) | |

(52) U.S. Cl.
CPC ............... *A61L 27/04* (2013.01); *A61L 27/18* (2013.01); *A61L 27/3834* (2013.01); *A61L 27/56* (2013.01); *A61L 27/58* (2013.01); *C12M 21/08* (2013.01); *C12M 25/14* (2013.01); *A61F 2002/0086* (2013.01); *A61F 2002/043* (2013.01); *A61F 2002/044* (2013.01); *A61F 2002/045* (2013.01); *A61F 2002/046* (2013.01); *A61F 2/90* (2013.01); *A61F 2210/0004* (2013.01); *A61F 2210/0076* (2013.01); *A61F 2230/0069* (2013.01); *A61F 2250/0067* (2013.01); *A61L 2430/22* (2013.01)

(56) References Cited

U.S. PATENT DOCUMENTS

| | | |
|---|---|---|
| 10,265,153 B2 | 4/2019 | La Francesca et al. |
| 2006/0085063 A1 | 4/2006 | Shastri et al. |
| 2010/0241214 A1 | 9/2010 | Holzer |
| 2011/0288654 A1 | 11/2011 | Badylak et al. |
| 2013/0018452 A1 | 1/2013 | Weitzner et al. |
| 2015/0086607 A1 | 3/2015 | Johnson |
| 2015/0282922 A1 | 10/2015 | Hingston |

| TIME OF MEASUREMENT | | TENSILE STRESS AT BREAK (MPA) | TENSILE STRAIN AT BREAK (%) | YOUNG'S MODULU (MPA) |
|---|---|---|---|---|
| PRE-IMPLANTATION (n=3) | MEAN | 7.25 | 397.38 | 2.44 |
| | SD | 0.59 | 5.52 | 0.24 |
| POST-IMPLANTATION (n=3) | MEAN | 4.43 | 408.61 | 1.72 |
| | SD | 0.77 | 17.64 | 0.09 |

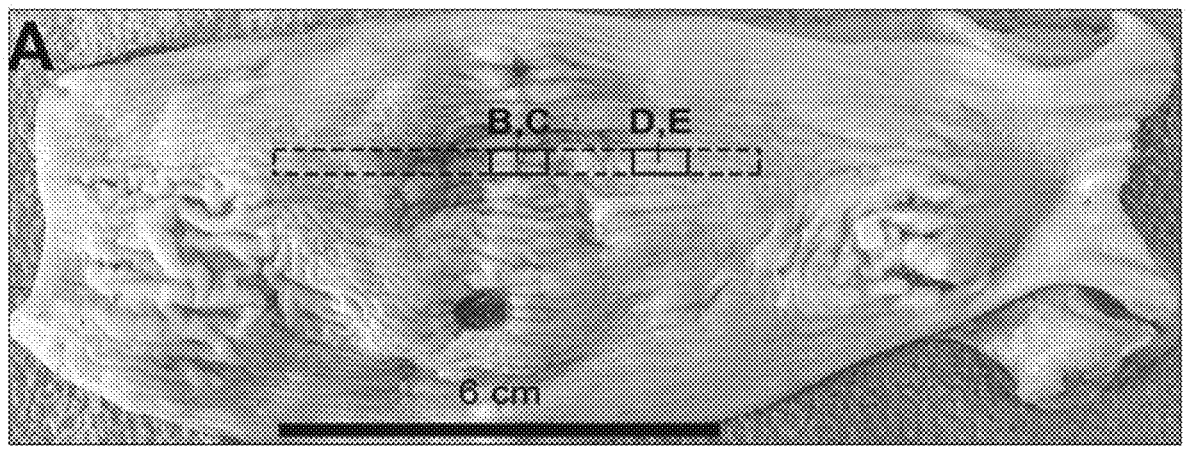
FIG. 14A
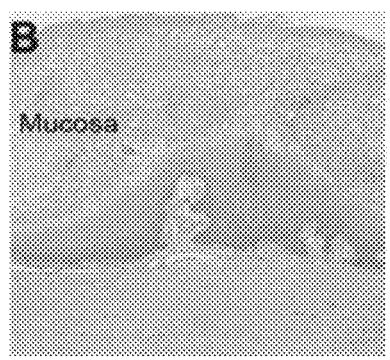　　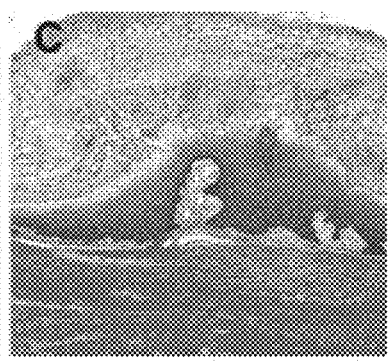
FIG. 14B　　　　　FIG. 14C
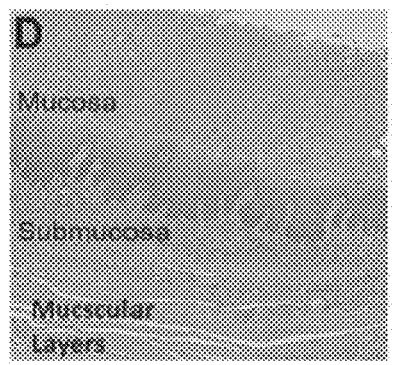　　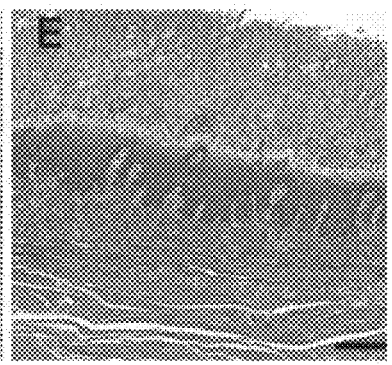
FIG. 14D　　　　　FIG. 14E

SYSTEMS AND METHODS FOR PRODUCING GASTROINTESTINAL TISSUES

CROSS-REFERENCE TO RELATED APPLICATION(S)

This application is a continuation of U.S. Non-provisional patent application Ser. No. 16/391,212 which is a continuation of U.S. Non-provisional patent application Ser. No. 15/350,970 filed Nov. 14, 2016 which claims priority to and the benefit of U.S. Provisional Patent Application Ser. No. 62/254,700 filed Nov. 12, 2015 and U.S. Provisional Patent Application Ser. No. 62/276,715 filed Jan. 8, 2016, the entire disclosure of which are both hereby incorporated by reference. This application is a continuation of U.S. Non-provisional application Ser. No. 16/020,053 filed Jun. 27, 2018 which claims priority to and the benefit of U.S. Provisional Patent Application Ser. No. 62/254,700 filed Nov. 12, 2015 and U.S. Provisional Patent Application Ser. No. 62/276,715 filed Jan. 8, 2016, the entire disclosure of which are both hereby incorporated by reference.

TECHNICAL FIELD

This disclosure relates to engineered tissues that are useful for replacement or repair of damage tissues.

BACKGROUND

Engineered biological tissues that are useful for replacement or repair of damaged tissues are often produced by seeding cells on synthetic scaffolds and exposing the cells to conditions that permit them to synthesize and secrete extracellular matrix components on the scaffold. Different techniques have been used for producing synthetic scaffolds, including nanofiber assembly, casting, printing, physical spraying (e.g., using pumps and syringes), electrospinning, electrospraying and other techniques for depositing one or more natural or synthetic polymers or fibers to form a scaffold having a suitable shape and size for transplanting into a subject (e.g., a human subject, for example, in need of an organ or region of engineered tissue).

It is estimated that over 500.000 individuals worldwide are diagnosed with esophageal malignancy each year. Congenital malformations of the esophagus, such as esophageal atresia, have an average prevalence of 2.44 per 10,000 births. Chronic esophageal stricture after esophageal injury is also common. While there have been advances in minimization of the extent of esophageal resection for early stage malignant disease, such as endoscopic mucosal resection, the mainstay of treatment for many esophageal disorders is surgical esophagectomy. Traditionally, autologous conduits such as stomach, small bowel, or colon are harvested and rerouted into the chest to restore gastrointestinal continuity. Many children with esophageal atresia or patients affected by either trauma or caustic injury to the esophagus ultimately undergo similar reconstruction. These treatment modalities are associated with high morbidity and mortality.

Autologous conduits are traditionally used because of the complex structure of the esophagus. Comprised of stratified squamous epithelium, submucosa and outer circular and longitudinal muscle layers, these multiple layers of the esophagus provide a barrier to contain oral intake and contamination from escape outside of the gastrointestinal tract. Furthermore, the combined layers provide a physiological mechanism for propulsion, and management of stresses during passage of the bolus either during swallowing or emesis.

It would be desirable to provide structure as well as a method of making a structure that can support tissue regeneration.

SUMMARY

Disclosed herein are implementations that pertain to synthetic scaffolds and related systems that enable production of gastrointestinal tissues (e.g., tissues of the esophagus, stomach, intestine, colon, or other hollow gastrointestinal tissue). In some embodiments, scaffolds provide guides for gastrointestinal (e.g., esophageal) tissue growth and regeneration in a subject. In some embodiments, the regenerated gastrointestinal tissue comprises muscle tissue, nervous system tissue, or muscle tissue and nervous system tissue. In some embodiments, gastrointestinal (e.g., esophageal) tissue is regenerated surrounding a scaffold. In some embodiments, the scaffold is not incorporated into the final regenerated tissue (e.g., the new esophageal tissue does not incorporate the scaffold into the regenerated esophageal walls). Accordingly, aspects of the disclosure relate to guided tissue regeneration where a scaffold provides support and/or signals that promote host tissue regeneration without the scaffold needing to be incorporated into the regenerated tissue (e.g., without the scaffold providing structural or functional support in the final regenerated tissue).

In some embodiments, a gastrointestinal (e.g., esophageal) scaffold includes biodegradable and/or bioresorbable material that is resorbed after gastrointestinal (e.g., esophageal) tissue regeneration is initiated (e.g., after functional esophageal tissue is regenerated).

In some embodiments, a gastrointestinal (e.g., esophageal) scaffold includes one or more structures that can be used to assist in removing the scaffold after gastrointestinal (e.g., esophageal) tissue regeneration is initiated (e.g., after functional esophageal tissue is regenerated).

In some embodiments, a scaffold is cellularized with one or more cell types prior to implantation. In some embodiments, the cells are autologous cells. In some embodiments, the cells are progenitor or stems cells. In some embodiments, the cells are obtained from bone marrow, adipogenic tissue, esophageal tissue, or other suitable tissue. In some embodiments, the cells can be obtained from various allogenic sources, including but not limited to sources such as amniotic fluid, cord bold and the like. In some embodiments, the cells are mesenchymal stem cells (MSCs)

In some embodiments, a scaffold is implanted at a site that provides a sufficient stem cell niche (e.g., an esophageal or other gastrointestinal site that provides a stem cell niche) for regenerating tissue in the subject. In some embodiments, without wishing to be bound by theory, the scaffold and/or cells that are provided on the scaffold help promote growth and/or regeneration of gastrointestinal tissue from host stem cells present at the site of scaffold implantation.

In some aspects, the disclosure relates to the discovery that growth of esophageal tissues can be promoted or enhanced by the presence of synthetic scaffolds that are engineered to replace or repair natural structural patterns and/or functional properties of diseased or injured tissues or organs, without the scaffolds becoming fully integrated into the final regenerated tissue. Thus, in some aspects, the disclosure provides a method for promoting or enhancing growth of gastrointestinal (e.g., esophageal) tissue, the method comprising: delivering to a gastrointestinal (e.g., esophageal) region of a subject a synthetic scaffold, wherein delivery of the synthetic scaffold results in growth of new gastrointestinal (e.g., esophageal) tissue in that region of the subject. In some embodiments, the diseased or injured gastrointestinal region is removed (e.g., surgically) prior to implanting the scaffold. In some embodiments, the scaffold is an approximately tubular structure that is implanted (e.g., sutured to the ends of the remaining gastrointestinal tissue after removal of the diseased or damaged tissue). In some embodiments, the implanted scaffold is shorter than the tissue that was removed (e.g., 5-50% shorter). In some embodiments, the remaining gastrointestinal tissue near the site of the implant is stretched when the tissue is attached (e.g., sutured) to the both ends of the scaffold. In some embodiments, new gastrointestinal (e.g., esophageal) tissue is regenerated over the implanted scaffold without being fully integrated with the scaffold. In some embodiments, the walls of the regenerated tissue do not incorporate the walls of the scaffold even though the scaffold can be retained within the lumen of the regenerated tissue. In some embodiments, the scaffold can be removed from the lumen formed by the regenerated tissue at a suitable point in the tissue regeneration process.

In some embodiments, the growth of new gastrointestinal (e.g., esophageal) tissue results in the formation of functional tissue (e.g., a functional esophagus) that does not require the continued presence of the scaffold for function.

In some embodiments, the synthetic scaffold is resorbable or dissolvable under physiological conditions. In some embodiments, the synthetic scaffold is removed from the gastrointestinal (e.g., esophageal) region of the subject after the formation of a functional esophagus.

In some embodiments, methods and compositions described herein also can be used for tracheal and/or bronchial tissue regeneration.

These and other aspects are described in more detail herein.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 14 A is a photograph of tissue of pig esophagus for histological analysis at 2.5 months post implantation with an embodiment of the scaffold as disclosed herein;

FIG. 14B is photograph of a magnified cross-sectional sample taken a section B of FIG. 14A illustrating the presence of mucosal tissue;

FIG. 14C is photograph of a magnified cross-sectional sample taken a section C of FIG. 14A illustrating the presence of mucosal tissue;

FIG. 14D is photograph of a magnified cross-sectional sample taken a section D of FIG. 14A illustrating the presence of mucosal and submucosa tissue and muscular layers;

FIG. 14E is photograph of a magnified cross-sectional sample taken a section E of FIG. 14A illustrating the presence of mucosal and submucosa tissue and muscular layers;

DETAILED DESCRIPTION

Figure 1A:
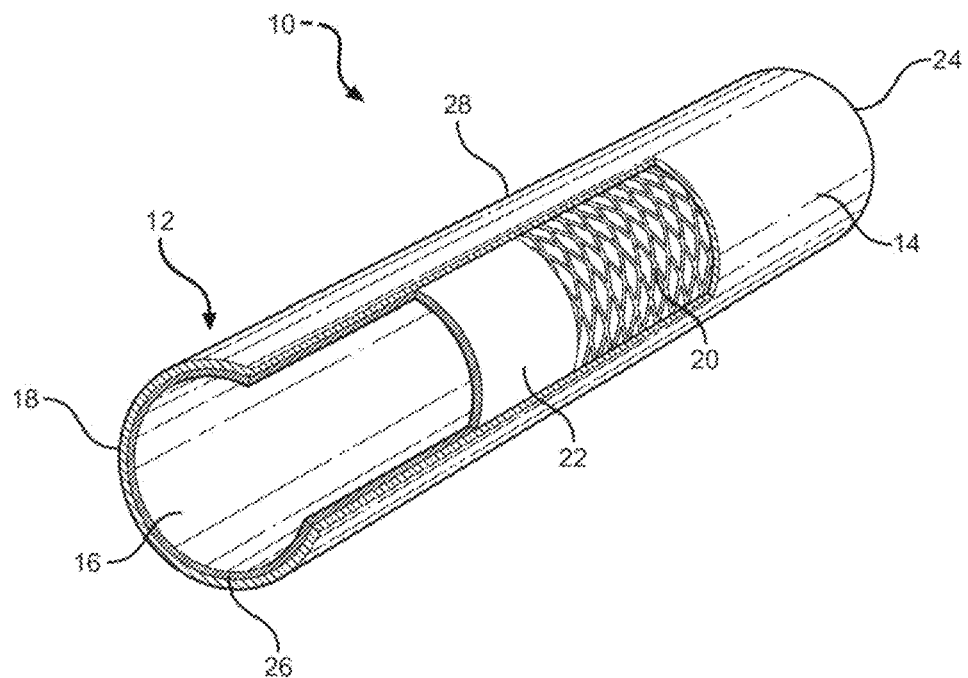
FIG. 1A is a perspective view of an embodiment of a synthetic scaffold as disclosed herein with a portion being rendered in partial cross-section.

Aspects of the disclosure relate in part to the remarkable discovery that inserting a synthetic scaffold into the esophageal region of a subject can promote or enhance the regeneration of new esophageal tissue (e.g., a complete and functional esophagus) in the subject without fully incorporating the scaffold into the regenerated tissue. Thus, in some embodiments, the disclosure provides a method for promoting or enhancing growth of gastrointestinal (e.g., esophageal) tissue, the method comprising: delivering to the gastrointestinal (e.g., esophageal) region of a subject a synthetic scaffold, wherein delivery of the synthetic scaffold results in growth of new gastrointestinal (e.g., esophageal) tissue in that region of the subject.

Tissue that is regenerated using methods described herein can be any gastrointestinal tissue, such as tissues of the esophagus, stomach, intestine, colon, rectum, or other hollow gastrointestinal tissue. In some aspects, the disclosure is based, in part, on the surprising discovery that methods described herein result in the regeneration of gastrointestinal tissue comprising muscle tissue, nervous system tissue, or muscle tissue and nervous system tissue.

In some embodiments, the synthetic scaffold is resorbable or dissolvable under physiological conditions (e.g., within a time period corresponding approximately to the time required for tissue regeneration). In some embodiments, at least a portion of the synthetic scaffold is resorbable or dissolvable under suitable physiological conditions.

In some embodiments, the synthetic scaffold is removed from the subject after the formation of a regenerated functional tissue (e.g., esophagus or portion thereof).

In some embodiments, a scaffold is designed to be readily retrievable by having a) one or more reversible attachments that can be easier to remove than a suture, for example to help disconnect the scaffold from the surrounding tissue (e.g., esophagus) after tissue regeneration, and/or b) one or more features that can be used to help retrieve the scaffold, for example after it has been disconnected from the surrounding tissue (e.g., adjacent esophageal tissue).

Non-limiting examples of reversible attachments include mechanical mechanisms (for example hooks and loops, connectors such as stents, or other mechanical attachments that can be disconnected) and/or chemical mechanisms (for example biodegradable or absorbable attachments and/or attachments that can be selectively removed by chemical or enzymatic means). In some embodiments, absorbable staples can be used. In some embodiments, absorbable staples comprise a co-polymer of polylactide-polyglycolide for example, or any other absorbable blend of material.

In some embodiments, surgical implantation and/or retrieval of a scaffold can be performed with thoracoscopic assistance.

Non-limiting examples of structural features that can assist in the retrieval or removal of a scaffold (e.g., after it is disconnected from the surrounding gastrointestinal tissue) include holes, indents, protrusions, or other structural features, or any combination thereof these structural features (e.g., FIG. 1A1, structural features 60) are located only on the outer surface of the scaffold. One or more of these structural features can be used to help grip or hold a tool (e.g. a grasper) that is being used to retrieve the scaffold. In some embodiments, one or more of these structural features can be located at only one end of the scaffold (e.g., the end that is proximal to the mouth of the subject). In some embodiments, one or more of these structural features can be located at both ends, or throughout the length of the scaffold. In some embodiments, one or more of these structural features are located only on the outer surface of the scaffold. In some embodiments, one or more of these structural features are located only on the inner surface of the scaffold. In some embodiments, one or more of these structural features are located on both the outer and inner surfaces of the scaffold. In some embodiments, a scaffold is reinforced (e.g., is thicker and/or includes stronger material) at or around the location of one or more structural features that are used to retrieve the scaffold.

In some embodiments, a disconnected scaffold can be removed endoscopically via the lumen of the airway leading to the esophagus. In some embodiments, a disconnected scaffold can be removed surgically In some embodiments, the subject has diseased (e.g., cancerous) or injured gastrointestinal tissue that needs to be replaced. In some embodiments, the subject is a human (e.g., a human patient).

In some embodiments, the disclosure provides engineered scaffolds that can be used to replace or repair an esophagus or a portion thereof. In some embodiments, esophageal scaffolds described herein may be used for promoting tissue regeneration (e.g., a regenerated esophagus or portion thereof) to replace a tissue in a subject (e.g., a human). For example, subjects (e.g., a human) having certain cancers (e.g., esophageal cancer) may benefit from replacement of a tissue or organ affected by the cancer. Without being to be bound by any particular theory, synthetic scaffolds described herein promote the growth of new tissue (e.g., esophageal tissue) in a subject and therefore provide a therapeutic benefit to the subject.

In some embodiments, the growth of new esophageal tissue results in the formation of a functional esophagus in the subject. In some embodiments, the new esophageal tissue does not incorporate the scaffold into the regenerated esophageal walls. In some embodiments, the scaffold is designed and manufactured to be absorbable and/or readily retrievable after the esophageal tissue has regenerated. In some embodiments, the scaffold is designed to be at least partially absorbable.

In some embodiments, a synthetic scaffold has a size and shape that approximates the size and shape of a diseased or injured gastrointestinal (e.g., esophageal) region that is being replaced.

In some embodiments, a scaffold will have at least two layers. The scaffold can have an approximately tubular structure in certain embodiments. FIG. 1A illustrates a non-limiting embodiment of a scaffold 10 having an approximately tubular body 12 having an interiorly oriented surface 14 and an exteriorly oriented surface 16. In some embodiments, a lateral cross-section of the scaffold 10 is approximately circular. In some embodiments, a lateral cross-section is approximately "D" shaped. However, scaffolds 10 having other cross-sectional shapes can be used. Scaffold 10 can have any suitable length and diameter depending on the size of the corresponding tissue being regenerated. In some embodiments, a scaffold 10 can be from around 1-10 cms in length (for example 3-6 cms, e.g., about 4 cms) in certain embodiments, or 10-20 cms long in other embodiments. However, it is contemplated that shorter or longer scaffolds 10 can be used depending on the application, needs of the patient and/or locations in the gastrointestinal tract requiring treatment. In some embodiments, a scaffold 10 can have an inner diameter of 0.5 to 5 cms. However, scaffolds with smaller or larger inner diameters can be used depending on the application, needs of the patient and/or locations in the gastrointestinal tract requiring treatment.

In some embodiments, the length of scaffold 10 can be shorter than the length of a gastrointestinal (e.g., esophageal) region being replaced. In some embodiments, the scaffold 10 has a length that is 50-95% (for example, about 50-60%, 60-70%, 70-80%, 80-90%, about 80%, about 85%, about 90%, or about 95%) of the length of the tissue being replaced. Without being bound to any theory, it is believed that certain regions of the associated gastrointestinal region can respond positively to traction force exerted on the associated organ tissue resulting the generation of certain bio-organically mediated signals that initiate or promote tissue growth and differentiation.

In certain embodiments, the length of scaffold 10 can have a length longer than the length of a gastrointestinal (e.g., esophageal) region being replaced. In some embodiments, the scaffold 10 has a length that is between 100% and 150% (for example, about 100-110%, 110-120%, 120-130%, 130-140%, about 100%, about 105%, about 110%, or about 115%) of the length being replaced. It is contemplated that the length of the scaffold will be that necessary to effectively replace the effected region. In certain situations, it is contemplated that a scaffold 10 will have a length that is longer than the replaced gastrointestinal region to effectively position the scaffold and reduce or minimize trauma and ischemia in the effected or associated regions.

In some embodiments, a scaffold 10 can be composed of a single layer of synthetic material. However, it is within the purview of this disclosure that the scaffold 10 also can include more than one layer of synthetic material.

Accordingly, in some embodiments, the synthetic scaffold 10 can be composed of multiple layers (e.g., 2 or more layers, for example 2, 3, 4, 5, or more layers). In some embodiments, one or more layers are made of the same material. In some embodiments, the different layers are made of different materials (e.g., different polymers and/or different polymer arrangements). Synthetic scaffolds 10 as disclosed herein may include two or more different components that are assembled to form the scaffold as it exists, e.g. prior to cellularization and/or implantation. In some embodiments, a synthetic scaffold 10 includes two or more layers that are brought into contact with each other, for example by the synthetic techniques that are used to manufacture the scaffold 10. In some embodiments, a scaffold 10 may be synthesized using a technique that involves several steps that result in two or more layers being brought together (e.g., the application of a layer of electrospun material onto a portion of the scaffold that was previously made, such as an prior layer of electrosprayed material, a prior layer of electrospun material, a surface of a different component (e.g., a braided tube or mesh) that is being incorporated into the scaffold, or a combination of two or more thereof).

In the embodiment as depicted in FIG. 1A, scaffold 10 includes at least one outer layer 18 that defines the outer surface 14 of the scaffold body 12. The scaffold 10 includes at least one additional inwardly oriented layer 20. In the embodiment as illustrated, the at least one additional inwardly oriented layer 20 is in direct contact with an inwardly oriented face of the outer layer 18. Where desired or required, the at least one inwardly oriented layer 20 can be configured to provide structural support to the associated scaffold body 12. In the embodiment depicted, in FIG. 1A, the at least one inwardly oriented layer 20 can be configured as a suitable mesh or braid positioned circumferentially around at least a portion of the longitudinal length of the scaffold body 12. In other embodiments, it is contemplated that the at least one inwardly oriented layer 20 can be composed of a suitable polymeric layer. In the embodiment as illustrated in FIG. 1A, the body 12 of scaffold 10 includes at least one layer 22 that is located interior to the mesh or braid layer 20.

Where desired or required, the scaffold 10 can have a wall thickness that is generally uniform. However, in some embodiments, the wall thickness can vary at specific regions of the body 12. In some embodiments, the wall thickness at one or both ends 24, 26 of the body 12 of scaffold 10 is different (e.g., thicker) than the walls of the central portion 28 of the scaffold 10 (not shown). In some embodiments, the thicker wall regions are stronger and provide greater support for sutures that are connected to one or both ends 24, 26 of the scaffold 10 when the scaffold is connected to surrounding gastrointestinal tissue. The thicker wall region(s) can also include discrete configurations that facilitate suturing. Non-limiting examples of such configurations include tubes, wholes, etc.

In certain embodiments, at least the exteriorly oriented surface 14 defined on the outwardly oriented layer 18 can be composed of an electrospun polymeric material. In certain embodiments, it is contemplated that the outwardly oriented wall 18 can be composed of electrospun polymeric material. In certain embodiments, the electrospun outwardly oriented layer can be in direct contact with a suitable braid material layer 20.

Fiber Orientation

Electrospun fibers can be isotropic or anisotropic. In some embodiments, fibers in different layers can have different relative orientations. In some embodiments, fibers in different layers can have substantially the same orientation. Fiber orientation can be altered in each layer of a composite or sandwich scaffold in addition.

In some embodiments, scaffolds with different porosities can be used. In some embodiments, one or more layers of a scaffold permit substantially complete cellular penetration and uniform seeding. In some embodiments, one or more layers of the scaffold may be constructed to prevent the penetration of one or more cell types, for example by densely packing the fibers. Controlling fiber diameter can be used to change scaffold porosity as the porosity scales with fiber diameter. Alternatively, blends of different polymers may be electrospun together and one polymer preferentially dissolved to increase scaffold porosity. The properties of the fibers can be controlled to optimize the fiber diameter, the fiber spacing or porosity, the morphology of each fiber such as the porosity of the fibers or the aspect ratio, varying the shape from round to ribbon-like. In some embodiments, the mechanical properties of each fiber may be controlled or optimized, for example by changing the fiber composition, and/or the degradation rate.

Figure 1B:
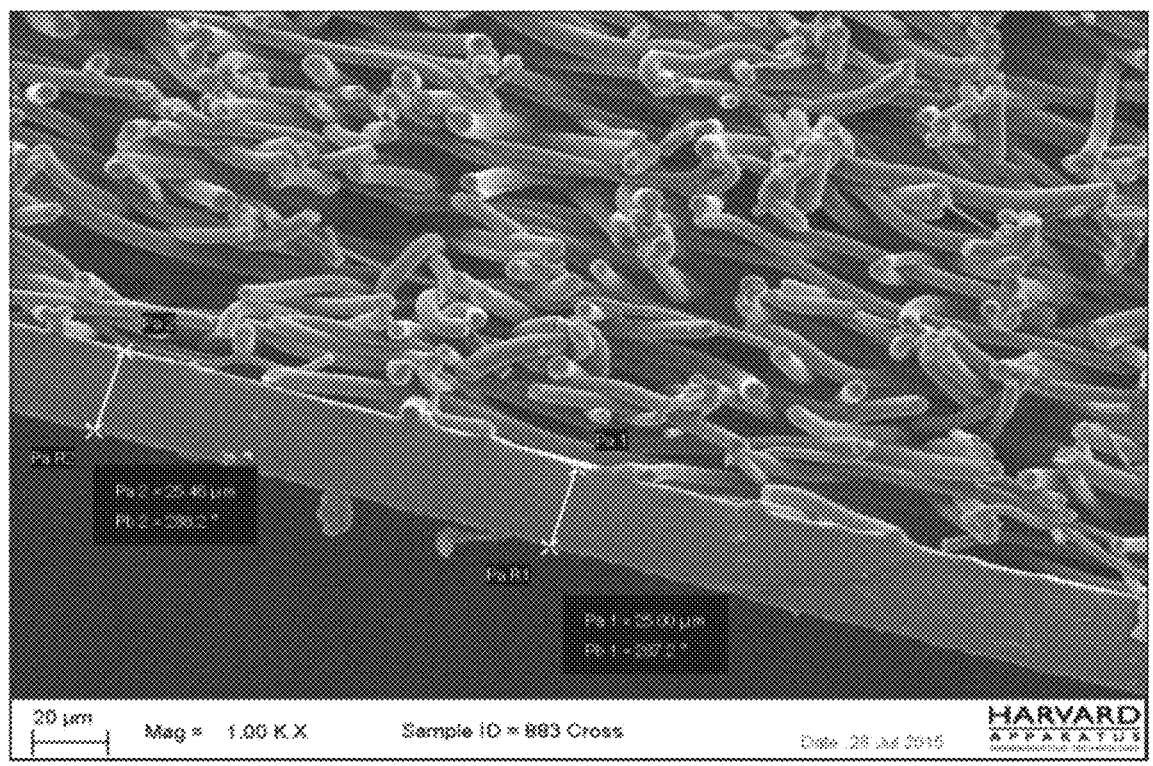
FIG. 1B is a photomicrograph of a surface of a tubing surface of an embodiment of the synthetic scaffold as disclosed herein.

In certain embodiments, the electrospun fiber material can provide a contoured surface such as a that depicted in FIG. 1B. In certain embodiments, at least one electrospun layer in scaffold 10 can be a polymeric fiber material such as polycarbonate polyurethane and can be produced by dissolving polycarbonate-polyurethane in a suitable solvent such as hexafluoroisopropanol (HFIP) that is spun and dried.

Figure 4A:
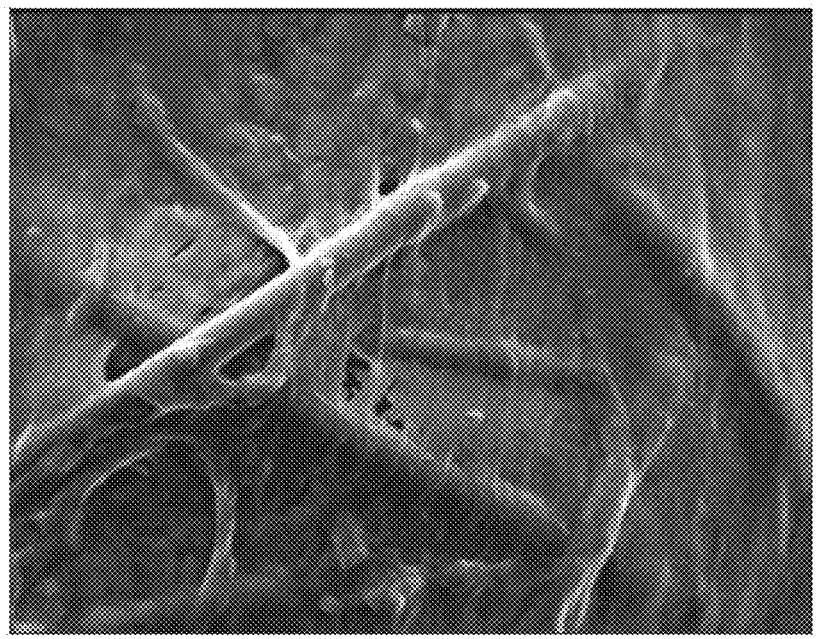
FIG. 4 A is a SEM photomicrograph of an outer surface region of an embodiment of the synthetic scaffold as disclosed herein showing cellular growth after seven days of bioreaction taken at 5000×.
FIG. 4B is a photomicrograph of an outer surface region of an embodiment of the synthetic scaffold as disclosed herein showing cellular growth after seven days of bioreaction.
Figure 4B:
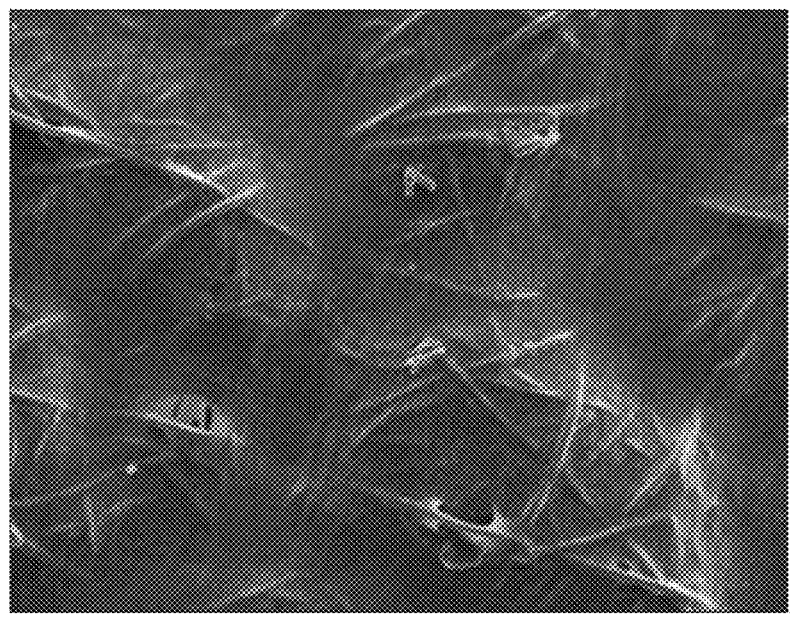
Figure 5:
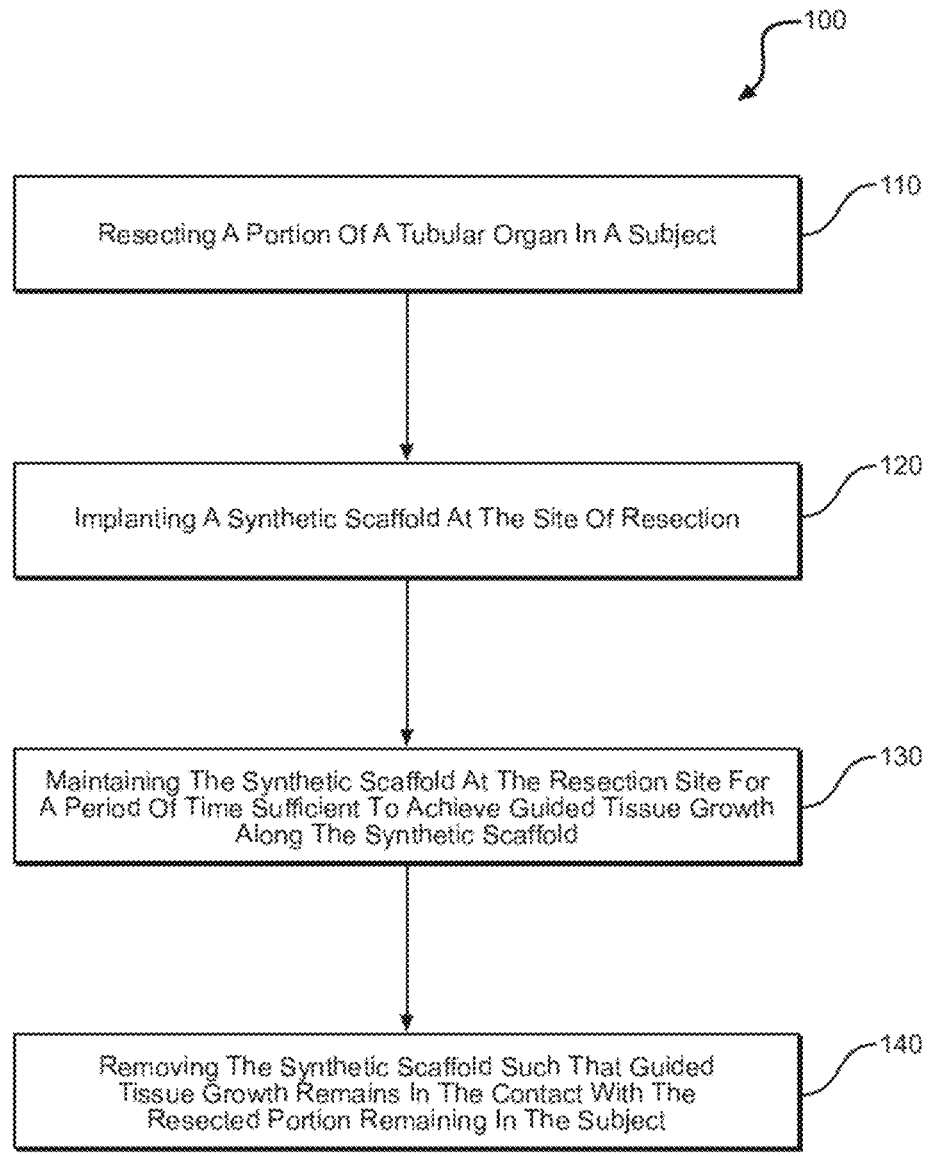
FIG. 5 is a process diagram of an embodiment an embodiment of the regeneration method as disclosed herein.

The spacing and porosity of the electrospun fiber material can be that such that cells seeded on the scaffold surface can adhere in suspended overlying relationship between respective fibers to permit the seeded cellular material to form sheets thereon as illustrated in FIGS. 4A and 4B.

Layering of Synthetic Scaffolds

Aspects of the disclosure relate to methods for producing synthetic scaffolds. In some embodiments, tubular synthetic scaffolds (e.g., a synthetic esophageal scaffold) are produced on a mandrel (e.g., by depositing material via electrospraying and/or electrospinning).

In some embodiments, one or more layers of a synthetic scaffold provide structural support to the scaffold, conferring a desired mechanical property to the scaffold. In some embodiments, a braided material (e.g., a braided tube, for example a nitinol braid, a PET braid, or a braid of other metallic or non-metallic material) can be inserted between two different layers of a scaffold to provide structural support. The compression force of the braided material (e.g., the force that the braid can exert on the next layer of material, for example the outer electrospun layer of material) can be controlled by controlling the pick count of the braid. In some embodiments, a braid can be coated (e.g., by dipping or other technique) in an organic solvent to help attach it to one or more other layers of the scaffold 10. In some embodiments, the length of the braid 20 does not extend to the ends of the scaffold body 12. In some embodiments, one or both ends of the scaffold 10 consist of two or more layers of material without a braided layer, whereas the central portion 28 of the scaffold body 12 includes an additional braided layer.

In some embodiments, one or more layers of a synthetic scaffold provide a barrier in the scaffold, creating a separation (e.g., a relatively impermeable separation) between an inner space (e.g., a luminal space) and an external space. In some embodiments, a barrier can be an electrosprayed polyurethane (PU) layer.

In some embodiments, different layers of a scaffold 10 can include one or more polymers (e.g., polyethylene terephthalate (PET), PU, or blends thereof). In some embodiments, a scaffold 10 can include a nitinol braid sandwiched between an inner PU layer (e.g., that was electrosprayed or electrospun onto a mandrel) and an outer PU layer (e.g., that was electrosprayed onto the braided material).

In certain embodiments the scaffold 10 can be formed using a scaffold support or mandrel. In some embodiments, a scaffold support or mandrel may be coated with a material (e.g., PLGA or other polymer) prior to depositing one or more layers of PU, PET, or a combination thereof.

In certain embodiments, the material in the braid or mesh layer can be composed of absorbable polymeric material.

Scaffold Production-Fiber Materials

In some embodiments, one or more layers of a scaffold may be constructed from fibrous material. In some embodiments, scaffolds comprise one or more types of fiber (e.g., nanofibers). In some embodiments, scaffolds comprise one or more natural fibers, one or more synthetic fibers, one or more polymers, or any combination thereof. It should be appreciated that different material (e.g., different fibers) can be used in methods and compositions described herein. In some embodiments, the material is biocompatible so that it can support cell growth. In some embodiments, the material is permanent, semi-permanent (e.g., it persists for several years after implantation into the host), or rapidly degradable (e.g., it is resorbed within several weeks or months after implantation into the host).

In some embodiments, the scaffold comprises or consists of electrospun material (e.g., macro or nanofibers). In some embodiments, the electrospun material contains or consists of PET (polyethylene terephthalate (sometimes written poly (ethylene terephthalate)). In some embodiments, the electrospun material contains or consists of polyurethane (PU). In some embodiments, the electrospun material contains or consists of PET and PU.

In some embodiments, the artificial scaffold may consist of or include one or more of any of the following materials: elastic polymers (e.g., one or more polyurethanes (PU), for example polycarbonates and/or polyesters), acrylamide polymers, Nylon, resorbable polysulfone polymers and mixtures thereof. In some embodiments, the scaffold may consist of or include polyethylene, polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinylalcohol in various degrees of hydrolysis (e.g., 87% to 99.5%) in cross-linked and non-cross-linked forms. In certain embodiments, the polymeric compound can also include compounds or processes to increase the hydrophilic nature of the polymer. In certain embodiments, this can involve incorporating compounds such as block copolymers based on ethylene oxide and propylene oxide. It is also contemplated that the hydrophilic nature of the polymer can be increase by suitable plasma treatment if desired or required.

In some embodiments, the scaffold may consist of or include block copolymers. In some embodiments, addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, and PET (polyethylene terephthalate (sometimes written poly(ethylene terephthalate))) can be solution spun or electrospun and combined with any other material disclosed herein to produce a scaffold. In some embodiments, highly crystalline polymers like polyethylene and polypropylene may be solution spun or combined with any other material disclosed herein to produce a scaffold.

In some embodiments, one or more polymers are modified to reduce their hydrophobicity and/or increase their hydrophilicity after the scaffold synthesis, but before scaffold cellularization and/or implantation.

The electrospun fibers can have a dimeter less than 10 micrometers in certain embodiments. In certain embodiments, the electrospun fibers. In certain embodiments, the electrospun fibers can have a diameter between 3 and 10 micrometers. The electrospun fibers can have a dimeter between 3 and 5 micrometers in certain embodiments.

In certain embodiments, it is contemplated that the material in the braid layer can be made in whole or in part of bioabsorbable materials such as PLGA and the like. it is also contemplated that, in certain configurations, the braid material can be loaded materials and compounds that can promote and/or support tissue growth and regeneration. Non-limiting examples of such compounds and materials include one or more of the following: antibiotics, growth factors and the like.

Electrospinning

In some embodiments, scaffolds are produced that include one or more layers (e.g., of PU and/or PET) produced via electrospinning. Electrospun material can be used for a variety of applications, including as a scaffold for tissue engineering. Appropriate methods of electrospinning polymers may include those described in Doshi and Reneker. Electrospinning process and application of electrospun fibers. J Electrostat. 1995; 35:151-60; Reneker D H, Chun I. Nanometer diameter fibers of polymer produced by electro spinning. Nanotechnology. 1996; 7:216-23; Dzenis Y. Spinning continuous fibers for nanotechnology. Science. 2004; 304:1917-19; or Vasita and Katti. Nanofibers and their applications in tissue engineering. Int J. Nanomedicine. 2006; 1(1): 15-30, the contents of which relating to electrospinning are incorporated herein by reference. Electrospinning is a versatile technique that can be used to produce either randomly oriented or aligned fibers with essentially any chemistry and diameters ranging from nm scale (e.g., around 15 nm) to micron scale (e.g., around 10 microns).

In some embodiments, electrospinning and electrospraying techniques used herein involve using a high voltage electric field to charge a polymer solution (or melt) that is delivered through a nozzle (e.g., as a jet of polymer solution) and deposited on a target surface. The target surface can be the surface of a static plate, a rotating drum (e.g., mandrel), or other form of collector surface that is both electrically conductive and electrically grounded so that the charged polymer solution is drawn towards the surface.

In some embodiments, the electric field employed is typically on the order of several kV, and the distance between the nozzle and the target surface is usually several cm or more. The solvent of the polymer solution evaporates (at least partially) between leaving the nozzle and reaching the target surface. This results in the deposition of polymer fibers on the surface. Typical fiber diameters range from several nanometers to several microns. The relative orientation of the fibers can be affected by the movement of the target surface relative to the nozzle. For example, if the target surface is the surface of a rotating mandrel, the fibers will align (at least partially) on the surface in the direction of rotation. In some cases, the nozzle can be scanned back and forth between both ends of a rotating mandrel.

In some embodiments, the size and density of the polymer fibers, the extent of fiber alignment, and other physical characteristics of an electrospun material can be impacted by factors including, but not limited to, the nature of the polymer solution, the size of the nozzle, the electrical field, the distance between the nozzle and the target surface, the properties of the target surface, the relative movement (e.g., distance and/or speed) between the nozzle and the target surface, and other factors that can affect solvent evaporation and polymer deposition.

Electrospinning and electrospraying processes may be used for producing interlinked polymer fiber scaffolds (e.g., hollow synthetic scaffolds) on a mandrel.

Support/Mandrel

In some embodiments, scaffold 10 (e.g., a scaffold having two or more layers) can be produced using a support (e.g., a solid or hollow support) on which the scaffold 10 can be formed. For example, a support can be an electrospinning collector, for example a mandrel, or a tube, or any other shaped support. It should be appreciated that the support can have any size or shape. However, in some embodiments, the size and shape of the support is designed to produce a scaffold that will support an artificial tissue of the same or similar size as the gastrointestinal tissue (or portion thereof) being replaced or supplemented in a host. It should be appreciated that a mandrel for electrospinning should have a conductive surface. In some embodiments, an electrospinning mandrel is made of a conductive material (e.g., including one or more metals). However, in some embodiments, an electrospinning mandrel includes a conductive coating (e.g., including one or more metals) covering a non-conductive central support.

It has been found quite unexpectedly that positioning suitable braid material to be integrated in the resulting scaffold 10 at a location proximate to the surface of the mandrel can serve as an aid to facilitate removal of the resulting scaffold 10 from contact with the mandrel.

Scaffold Properties

It should be appreciated that aspects of the disclosure are useful for enhancing the physical and functional properties of any scaffold, for example a scaffold based on electrospun and/or electro sprayed fibers. In some embodiments, one or more scaffold components can be thin sheets, cylinders, thick ribs, solid blocks, branched networks, etc., or any combination thereof having different dimensions. In some embodiments, the dimensions of a complete and/or assembled scaffold are similar or identical to the dimension of a tissue or organ being replaced. In some embodiments, individual components or layers of a scaffold have smaller dimensions. For example, the thickness of a nanofiber layer can be from several nm to 100 nm, to 1-1000 microns, or even several mm. However, in some embodiments, the dimensions of one or more scaffold components can be from about 1 mm to 50 cms. However, larger, smaller, or intermediate sized structures may be made as described herein.

In some embodiments, scaffolds are formed as tubular structures that can be seeded with cells to form tubular tissue regions (e.g., esophageal, or other tubular regions). It should be appreciated that a tubular region can be a cylinder with a uniform diameter. However, in some embodiments, a tubular region can have any appropriate tubular shape (for example, including portions with different diameters along the length of the tubular region). A tubular region also can include a branch or a series of branches. In some embodiments, a tubular scaffold is produced having an opening at one end, both ends, or a plurality of ends (e.g., in the case of a branched scaffold). However, a tubular scaffold may be closed at one, both, or all ends, as aspects of the invention are not limited in this respect. It also should be appreciated that aspects of the invention may be used to produce scaffolds for any type or organ, including hollow and solid organs, as the invention is not limited in this respect. In some embodiments, aspects of the invention are useful to enhance the stability of scaffold or other structures that include two or more regions or layers of fibers (e.g., electrospun nanofibers) that are not physically connected.

In some embodiments, a scaffold is designed to have a porous surface having pores ranging from around 10 nm to about 100 micron in diameter that can promote cellularization. In some embodiments, pores have an average diameter of less than 50 microns, less than 40 microns, less than 30 microns, less than 20 microns or less than 10 microns (e.g., approximately 5, approximately 10, or approximately 15 microns). In some embodiments, pores have an average diameter of 20-40 microns. In some embodiments, pore size is selected to prevent or reduce an immune response or other unwanted host response in the subject. Pore sizes can be estimated using computational and/or experimental techniques (e.g., using porosimetry). However, it should be appreciated that pores of other sizes also can be included.

In some embodiments, a surface layer of a scaffold is synthesized using fibers that include one or more dissolvable particles that can be dissolved during or after synthesis (e.g., by exposure to a solvent, an aqueous solution, for example, water or a buffer) to leave behind pores the size of the dissolvable particles. In some embodiments, the particles are included in the polymer mix that is pumped to the nozzle of an electrospinning device. As a result, the particles are deposited along with the fibers. In some embodiments, the electrospinning procedure is configured to deposit thick fibers (e.g., having an average diameter of several microns, about 10 microns, and thicker). In some embodiments, if the fibers are deposited in a dense pattern, one or more fibers will merge prior to curing to form larger macrostructures (e.g., 10-100 microns thick or more). In some embodiments, these macrostructures can entangle two or more layers of fibers and or portions (e.g., fibers) from two or more different components of a scaffold thereby increasing the mechanical integrity of the scaffold. In some embodiments, when such macrostructures are formed (e.g., via electrospinning as described herein) at one or more stages during scaffold synthesis (e.g., to connect two or more layers and/or components), the surface of the macrostructure(s) can be treated (e.g., etched or made porous using dissolvable particles as described herein) in order to provide a surface suitable for cellularization.

In some embodiments, the amount of flexible scaffold material (e.g., the slack) between two or more structural components (e.g., rings), between structural members (e.g., arcuate members) of a single continuous structural component, and/or of a braided support material can be used to determine the mechanical properties (e.g., tensile strength, elongation, rotation, compression, range of motion, bending, resistance, compliance, degrees of freedom, elasticity, or any other mechanical property, or a combination thereof) of a synthetic scaffold.

In certain embodiments, the scaffold 10 can also include a cellular sheath derived from cells seeded on the outer surface of the scaffold during incubation. The cellular sheath adheres to and is in overlying relationship to the outer surface of the scaffold. It is contemplated that a major portion of the cells present in the cellular sheath will be connected to the outermost surface of the outer surface and will span pores (e.g., FIG. 1A1, pores 50) defined therein to form a continuous or generally continuous surface.

In certain embodiments, the cellular sheath can have a thickness sufficient to provide structural integrity to the sheath layer. In certain embodiments, the cellular sheath will be composed of a number of cells which are in contact with the external surface of the scaffold sufficient to direct regenerating cells in contact with the sheath to produce a tissue wall that overlays the sheath but does not integrate therewith. In certain embodiments, the sheath can be composed of a lining that is between 1 and 100 cells thick on average. Certain embodiments can have a cell thickness between 10 and 100; between 10 and 30; between 20 and 30, between 20 and 40; between 20 and 50; between 10 and 20; between 30 and 50; between 30 and 60; between 40 and 60; between 40 and 70; between 70 and 90.

The scaffold 10 with the associated cellular sheath provides a moveable insertable device that can be positioned in a suitable gastrointestinal resection site. The scaffold 10 with the associated cellular sheath in contact therewith can be transported to the desired resection site for implantation. In certain embodiments, the scaffold 10 is configured to be removable from the implantation site after suitable regeneration of the resected organ. In certain embodiments, the removed scaffold will include some or all of the cellular sheath connected thereto.

Also disclosed is are various embodiments of method of regenerating a tubular organ such as a gastrointestinal organ. In certain embodiments, the method 100 includes the step of resecting a that comprises resecting a portion of a tubular organ in a subject as at reference numeral 110. The organ to be resected can be a tubular organ of the gastrointestinal tract that has been damaged or compromised by disease injury, trauma or congenital conditions. In certain embodiments, non-limiting examples of suitable organs include one of the esophagus, rectum and the like. In certain embodiments, suitable organs include at least one of the esophagus, small intestines, colon, rectum.

The resection can be achieved by any suitable surgical procedure and produced a resected organ portion that remains connected to the gastrointestinal tract and remains in the subject after resection. The resection operation can yield suitable resection edges in certain embodiments.

After resection is completed, a synthetic scaffold is implanted at the site of the resection as at reference numeral 120. In certain embodiments, implantation can include the step of connecting the respective ends of the resected organ as it remains in the subject to respective ends of the synthetic scaffold such that the synthetic scaffold and at the resected organ can achieve a suitable junction between the respective members. This can be achieved by one or more of sutures, bioorganic tissue glue, etc.

In certain embodiments, the synthetic scaffold that is implanted can be a tubular member that has an outer polymeric surface and a cellularized sheath layer (e.g., FIG. 1A1, cellularized sheath layer 40) overlying at least a portion of the of the outer polymeric surface. Various embodiments of the synthetic scaffold have been discussed and can be employed and utilized in the method disclosed herein. In certain embodiments, the synthetic scaffold will include a first end and a second end opposed to the first end, an outer polymeric surface positioned between the first end and the second end and a cellularized sheath layer overlying at least a portion of the outer polymeric surface. In certain embodiments, the implantation step can be one that brings at least a portion of the cellularized sheath layer into proximate contact with to at least one of the resection edges of the resected organ portion.

In certain embodiments, the method as disclosed herein also includes the step of maintaining the synthetic scaffold at the resection site for a period of time sufficient to achieve guided tissue growth along the synthetic scaffold as at reference numeral 130. In certain embodiments, the guided tissue growth is derived from and is in contact with the tissue present in the resected organ portion remaining in the subject. In certain embodiments, the guided tissue growth will be contiguous with the associated regions of the resected organ. In certain embodiments, the guided tissue growth will exhibit differentiated tissue. In certain embodiments, the guided tissue growth will parallel the outer surface of the cellularized sheath layer at a position outward thereof. In certain embodiments, the guided tissue growth is derived from and is in contact with the tissue present in the resected organ portion remaining in the subject and will be contiguous with the associated regions of the resected organ. The guided tissue growth will exhibit differentiated tissue growth and can be parallel the outer surface of the cellularized sheath layer at a position outward thereof.

After the guided tissue growth has been achieved, the process 100 as disclosed herein can include step of removing the synthetic scaffold as at reference numeral 140. In certain embodiments, the removing step occurs in a manner such that the guided tissue growth remains in the contact with the resected portion of the organ remaining in the subject. In certain embodiments, the removal process can include intrascopically removing the synthetic scaffold from the interior of the guided tissue growth.

In certain embodiments, the synthetic scaffold can be constructed in whole or in part from bioabsorbable polymeric material. In such situations, the method as disclosed herein can include the step of maintaining contact between the synthetic scaffold and the resection edge for an intervals sufficient to achieve guided tissue growth along the synthetic scaffold such that at least a portion of the synthetic scaffold is absorbed at the site of resection within a period of time sufficient to achieve guided tissue growth along the synthetic scaffold. In certain embodiments where the scaffold is composed entirely of bioabsorbable material, the scaffold will be configured to maintain structural integrity during guided tissue growth. In certain embodiments, where the synthetic scaffold is composed of bioabsorbable material in selected regions, it is contemplated that the remainder of the scaffold can be removed by suitable procedures after the guided tissue growth has been achieved.

Guided tissue growth can be monitored by suitable means. In certain embodiments, tissue growth can be monitored endoscopically.

In certain embodiments of the method as disclosed herein, the method can also include the step of imparting cellular material onto the polymeric surface of the synthetic scaffold and allowing the cellular material to grow to form the cellular sheath layer, the imparting and allowing steps occurring prior to the resecting step.

In certain embodiments, the synthetic scaffold that is employed in the method disclosed herein a tubular member where the outer surface includes spun polymeric fibers. In certain embodiments, the spun fibers can be electrospun by suitable methods such as those described in this disclosure. The cellularized sheath layer spans at least a portion outwardly positioned electrospun fibers in certain embodiments. The cellularized sheath layer can is composed of cellular material, the cellular material including at least one of mesenchymal cells, stem cells, pluripotent cells. The cellular material can be autologously derived from the subject or can be allogenically derived.

Figure 11A:
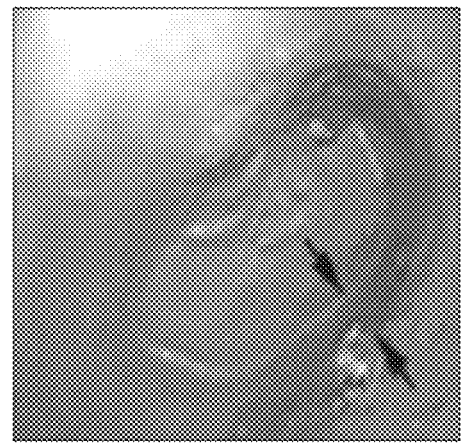
FIG. 11A is a photograph of regenerated tissue located on the interior of regenerated tubular tissue at an esophageal resection site of a first test subject taken after removal of an embodiment of the scaffold device as disclosed herein at 3 to 4 weeks post-surgery.
Figure 11B:
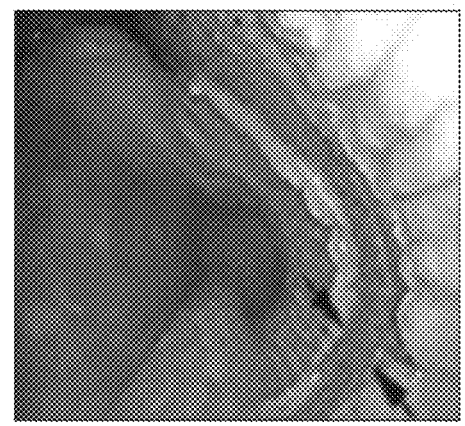
FIG. 11B is a photograph of regenerated tissue that is located on the interior of the esophagus at the esophageal resection site of FIG. 11A at an intermediate interval after removal of the scaffold device showing tissue growth.
Figure 11C:
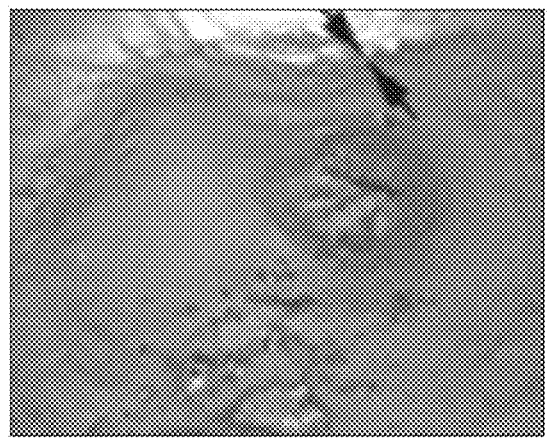
FIG. 11C is a photograph of regenerated tissue that is located on the interior of the esophagus at the esophageal resection site of FIG. 11A at an interval subsequent to the intermediate interval of FIG. 11B showing tissue growth.
Figure 12A:
FIG. 12A is a photograph of regenerated tissue located on the interior of regenerated tubular tissue at an esophageal resection site of a second test subject taken after removal of an embodiment of the scaffold device as disclosed herein at 3 to 4 weeks post-surgery.
Figure 12B:
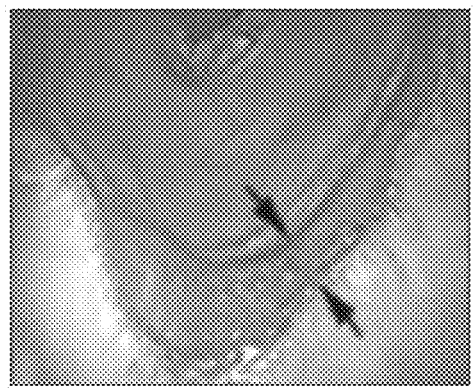
FIG. 12B is a photograph of regenerated tissue that is located on the interior of the esophagus at the esophageal resection site of FIG. 12A at an intermediate interval after removal of the scaffold device showing tissue growth.
Figure 12C:
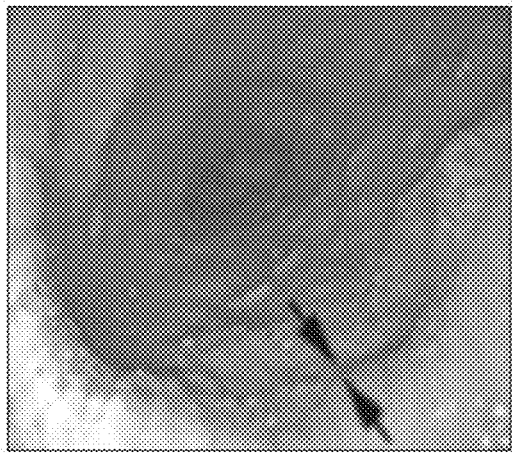
FIG. 12C is a photograph of regenerated tissue that is located on the interior of the esophagus at the esophageal resection site of FIG. 12A at an intermediate interval after removal of the scaffold device showing tissue growth subsequent to the tissue growth depicted in FIG. 12B.
Figure 12D:
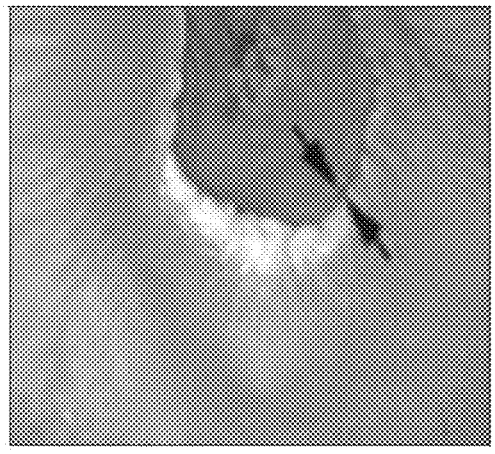
FIG. 12D is a photograph of regenerated tissue that is located on the interior of the esophagus at the esophageal resection site of FIG. 12A at an intermediate interval after removal of the scaffold device showing tissue growth subsequent to the tissue growth depicted in FIG. 12C.
Figure 12E:
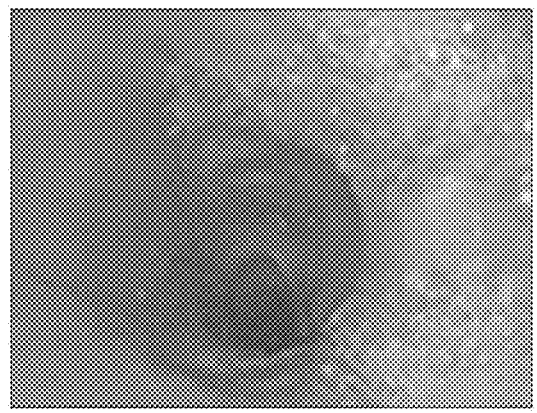
FIG. 12E is a photograph of regenerated tissue that is located on the interior of the esophagus at the esophageal resection site of FIG. 12A at an intermediate interval after removal of the scaffold device showing tissue growth subsequent to the tissue growth depicted in FIG. 12D.

Without being bound to any theory, it is believed that implanting a synthetic scaffold such as those as variously disclosed herein, particularly one seeded with an overlying cellular sheath, promotes growth, regeneration and differentiation of the subject tissue in contact with or proximate to the location of the implanted synthetic scaffold. The growing regenerating tissue is guided by the synthetic scaffold and associated sheath to produce a tubular cellular body that is integrally connected to the resected ends of the remaining tubular organ and outwardly flaring to encapsulate the synthetic scaffold and associated cellular sheath layer. It is believed that the scaffold and associated cellular sheath layer may promote or stimulate regenerative growth of the resected tissue while minimizing tissue rejection responses. It is also believed that the presence of the cellular sheath layer can reduce or minimize penetration of the regenerated tissue into the sheath layer during growth and differentiation. In certain embodiments, tissue generation proceeds from the respective ends toward the middle. Once the regenerated tissue is in position, the synthetic scaffold can be removed. In certain embodiments, immediately after the removal of the synthetic scaffold, the regenerated tissue structure will lack the inner epithelial layer. This layer has been seen to regenerate after removal of the scaffold as illustrated in FIGS. 11A, 11B and 11C taken immediately after scaffold removal, 2 months post removal and 3 months post removal respectively.

In order to further understand the present disclosure, reference is made to the following Examples. These Examples are included for purposes of illustration and are to be considered illustrative of the present disclosure and the invention as set forth in the claims.

EXAMPLES

Example 1: Esophageal Scaffolds

Figure 1C:
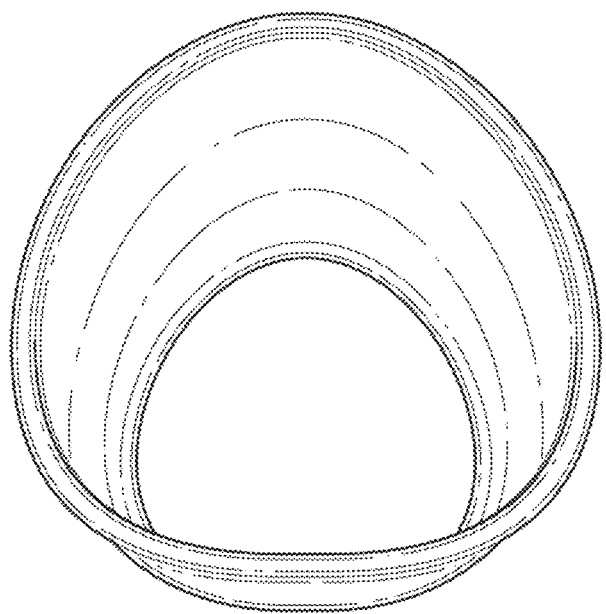
FIG. 1C side perspective view of a second embodiment of a synthetic scaffold as disclosed herein.

Synthetic esophageal scaffolds were produced containing three layers of material as illustrated in FIG. 1A. A first layer of polyurethane (PU) was deposited onto a metallic mandrel via electrospraying. A braided material was then deposited on the first PU layer. A second PU layer was then deposited via electrospinning. The resulting scaffolds were then removed from the mandrel. Each scaffold defined a tubular structure having a wall that included three layers (a braided layer sandwiched between and inner electro sprayed layer and an outer electrospun layer). Physical dimensions of the scaffold were determined by scanning electron microscopy (SEM). The average scaffold wall thickness was approximately 500 microns. A non-limiting SEM view of a cross-section of the wall is shown in FIG. 1B. A non-limiting visual image of a cross-section of the tubular scaffold is shown in FIG. 1C. This image shows that the cross-section is approximately "D" shaped. This can be obtained by using a mandrel that has a "D" shaped cross section.

The outer electrospun layer was a layer of polymer fibers defining pores. The average fiber diameter in the outer layer was approximately 3-6 microns The average pore size was approximately 15-20 microns, and the median pore size was approximately 25-45 microns.

Scaffolds were attached to a support capable of rotating in a bath of liquid medium within a bioreactor chamber. The rotating mechanism can include magnetic drives that allow the support along with the attached scaffold to be rotated around its longitudinal axis within the liquid bath.

Scaffolds were seeded with cells (e.g., MSCs or other stem cells) by depositing cell solutions on the external scaffold surface. The seeded scaffolds were then incubated in liquid media that supports cell growth by rotating the scaffolds in a bath of the liquid media within a bioreactor chamber for approximately one week. The resulting scaffolds include a cellular sheath that is in overlying relationship to the outer surface of the scaffold. In certain embodiments, the cellular sheath can have a thickness sufficient to provide structural integrity to the sheath layer. In certain embodiments, the cellular sheath will be composed of a number of cells which are in contact with the external surface of the scaffold sufficient to direct regenerating cells in contact with the sheath to produce a tissue wall that overlays the sheath but does not integrate therewith. In certain embodiments, the sheath can be composed of a lining that is between 1 and 100 cells thick on average. Certain embodiments can have a cell thickness between 10 and 100; between 10 and 30; between 20 and 30, between 20 and 40; between 20 and 50; between 10 and 20; between 30 and 50; between 30 and 60; between 40 and 60; between 40 and 70; between 70 and 90.

The scaffold 10 having the seeded cellular sheath can be implanted in to the resection site and can be positioned in place. It is contemplated that the seeded cells present in the sheath can continued to grow post implantation. In such situations, the seeded cells present in the sheath will maintain and support a structure that is separate from and tandem to the tissue regenerating at the implantation site.

The respective scaffolds were then implanted into esophageal sites in pigs. An approximately 5 cm section of esophagus was removed and replaced with a scaffold section that was sutured to the ends of the remaining esophageal tissue in the subject.

The regeneration of esophageal tissue was monitored endoscopically for several weeks.

Figure 2:
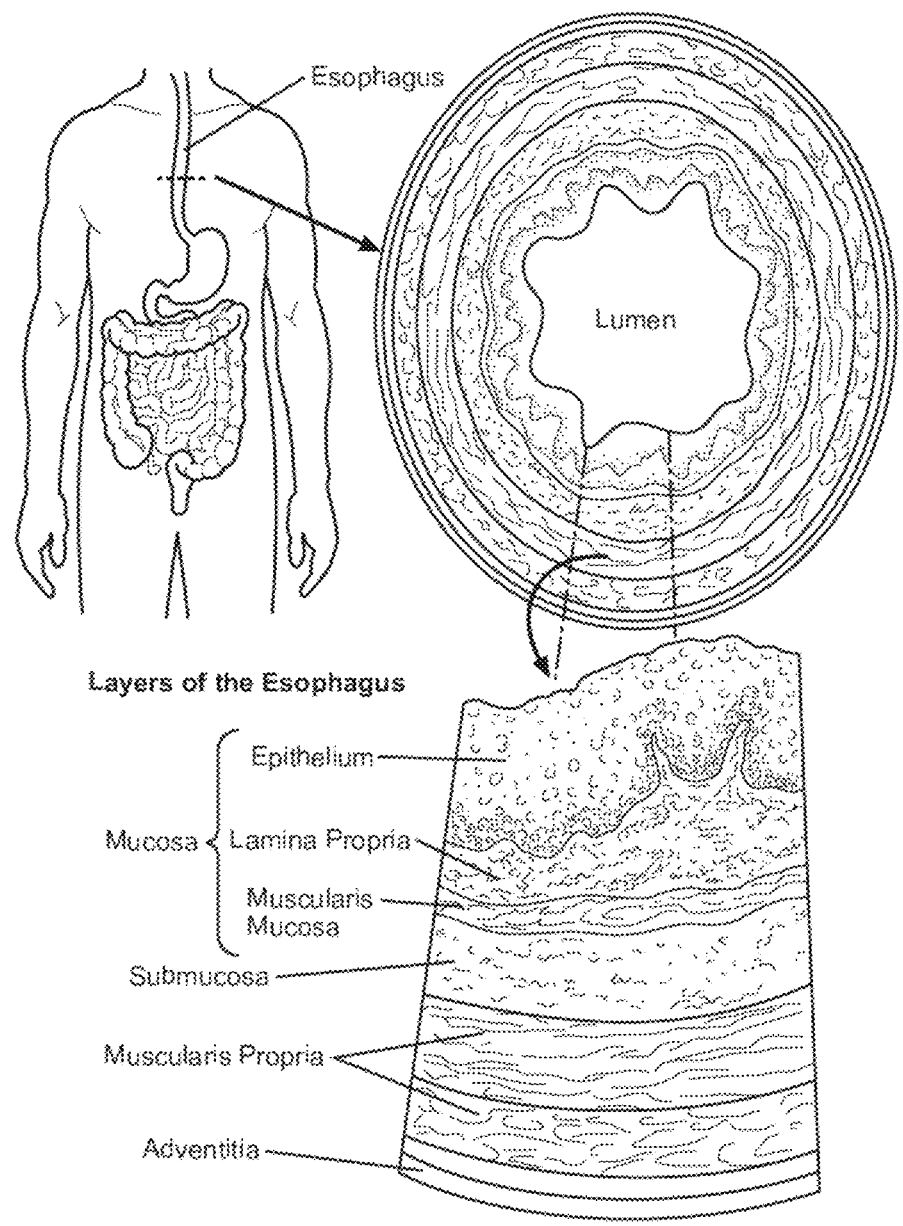
FIG. 2 is a non-limiting depiction of the biological layers of an esophagus.

The esophagus is a long muscular tube that has cervical, thoracic, and abdominal parts. FIG. 2 is a diagram that illustrates a cross-section of an esophagus in a human. In an adult human the esophagus can be 18 cm to 25 cm in length. An esophagus wall is composed of striated muscle in the upper part, smooth muscle in the lower part, and a mixture of the two in the middle. Accordingly, provided herein, in some embodiments, are multilayered synthetic scaffolds that can promote repair and regeneration of esophageal tissue having two or more layers corresponding to natural esophageal tissue layers.

Figure 3:
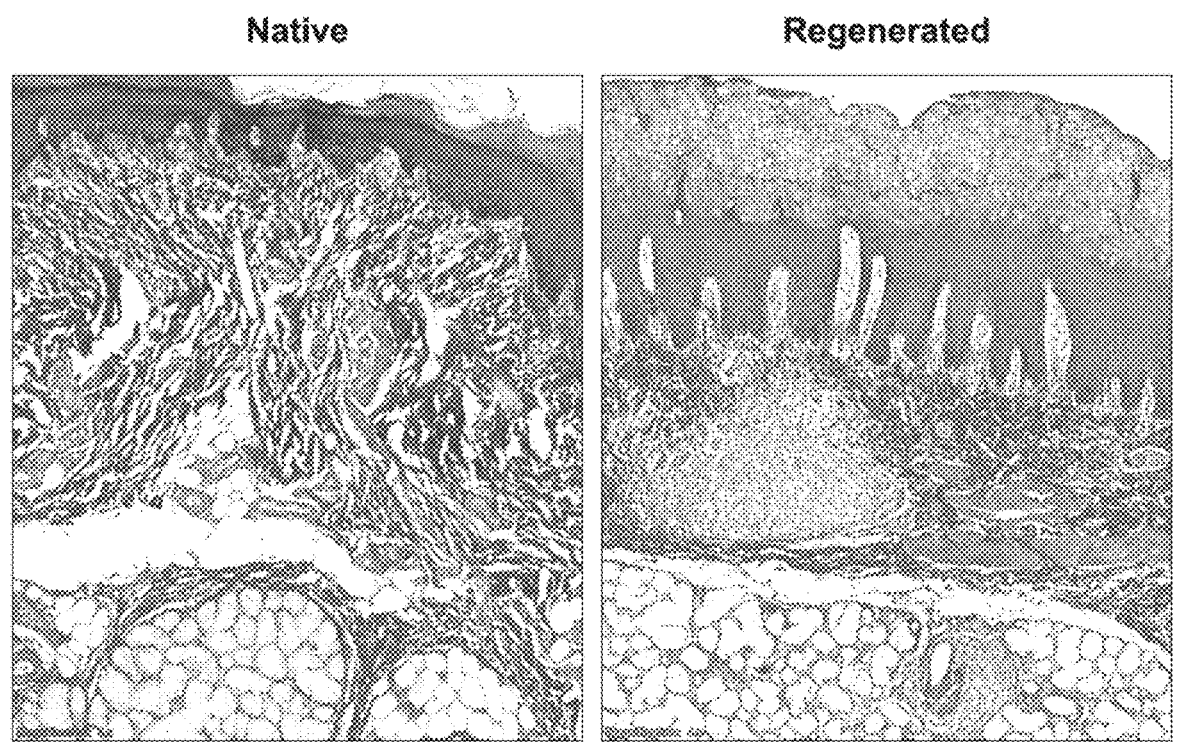
FIG. 3 illustrates a non-limiting example of regenerated esophageal tissue in comparison with corresponding native tissue.

FIG. 3 shows stained cross-sections of native and regenerated esophageal tissue 1-2 weeks after an esophageal scaffold implant in a pig. The cross section shows regeneration of essentially all the esophageal tissue layers (including different muscle and gland layers). Further analysis of the regenerated tissue revealed that the scaffold itself was not incorporated into the regenerated esophageal wall. The scaffold was still present within the esophagus, but appeared to have acted as a guide that stimulated esophageal regeneration as opposed to becoming an integral part of the regenerated esophagus.

Example II: Esophageal Implant

Synthetic esophageal scaffolds were produced that contained three layers as illustrated in FIG. 1A with the outer electrospun layer of poly-carbonate-polyurethane being deposited as a solution of polycarbonate polyurethane dissolved in Hexafluoroisopropanol (HFIP) (DuPont, Wilmington, DE, USA) at 12% w/v. The electrospinning apparatus used was commercially available from IME Technologies, Geldrop, Netherlands. The electrospun fibers were collected on a target aluminum mandrel rotating at 800 rpm and placed at a distance of 22 mm from the syringe tip to deposit an isotropic fiber to produce a scaffold having an average wall thickness of 500 microns. The scaffolds were dried in a vacuum to remove residual solvent. The scaffolds were then plasma treated with 2 consequent cycles of ethylene and oxygen gases using a low pressure plasma system (Diener Tetra 150-LF-PC-D). Scaffolds were gamma sterilized (STERIS, Northborough, MA). The applied dose range was 25-35 KGy.

The resulting tubes were polymeric scaffolds composed of electrospun polyurethane having a consistent outer diameter (OD) of 22 mm and a length of 11 cm.

Figure 7A:
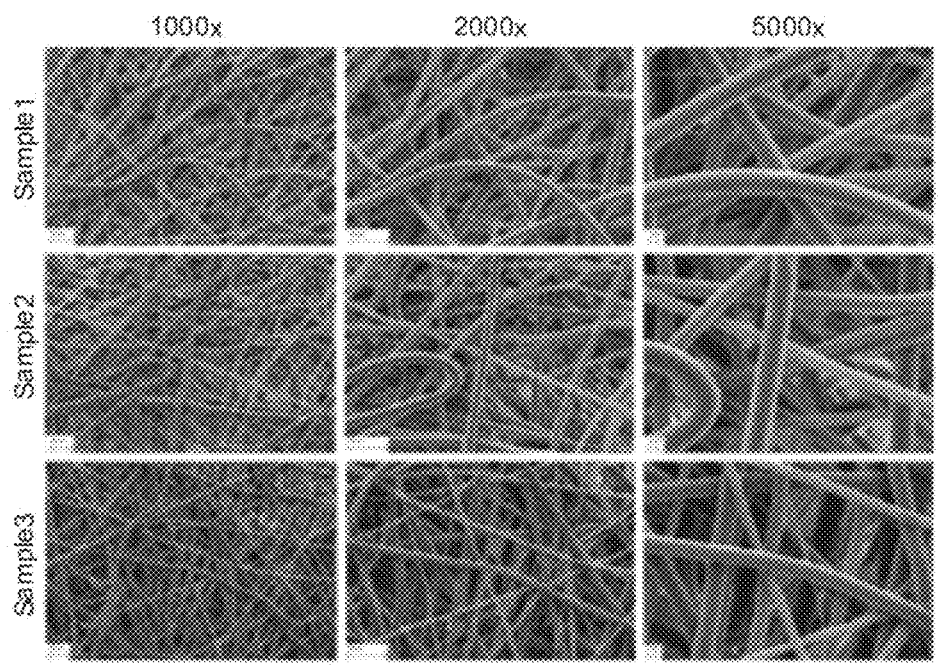
FIG. 7A is are SEMs of samples of an electrospun scaffold according to an embodiment as disclosed herein taken at 1000×, 2000× and 5000× respectively.

The morphology of the electrospun fibers was analyzed by scanning electron microscopy (Zeiss-EVO MA10). Samples of the scaffolds were sputter coated with Platinum and Palladium using a sputter coater for two minutes (Cressington-208HR, TED PELLA, Inc, Redding, CA) under a pressure of $8 \times 10^{-2}$ mbar and an electric potential of 300 V. Porosity was calculated using gravimetric measurements. Porosity, $\varepsilon$, is defined in terms of the apparent density of the fiber mat, $\rho APP$ and bulk density of the polymer, $\rho PU$ of which it is made: $\varepsilon = 1 - \rho APP/\rho PU$. The apparent scaffold density $\rho APP$ was measured as mass to volume ratio on 10 mm dry disks: $\rho APP = Mass/VPU$. Pore size measurements were taken using a mercury porosimeter system (Micromeritics AutoPore IV). Tensile tests on were performed consistent with ASTM D638 guidelines on 10 mm×40 mm samples that were mounted on an electromechanical load frame (Instron 5943 Apparatus) using a 1 kN load cell. The testing parameters were the same for all samples, at a 100 Hz data acquisition rate, a gauge length of 30 mm, and a test speed of 1 mm/sec. Scanning electron microscopy at increasing magnifications as illustrated in FIG. 7A demonstrated the isotropic fiber arrangement aspects of the electrospun synthetic scaffold. The smooth surface and isotropic nature of the fibers insures strength and elasticity of the scaffold is uniform in all directions.

Figure 7B:
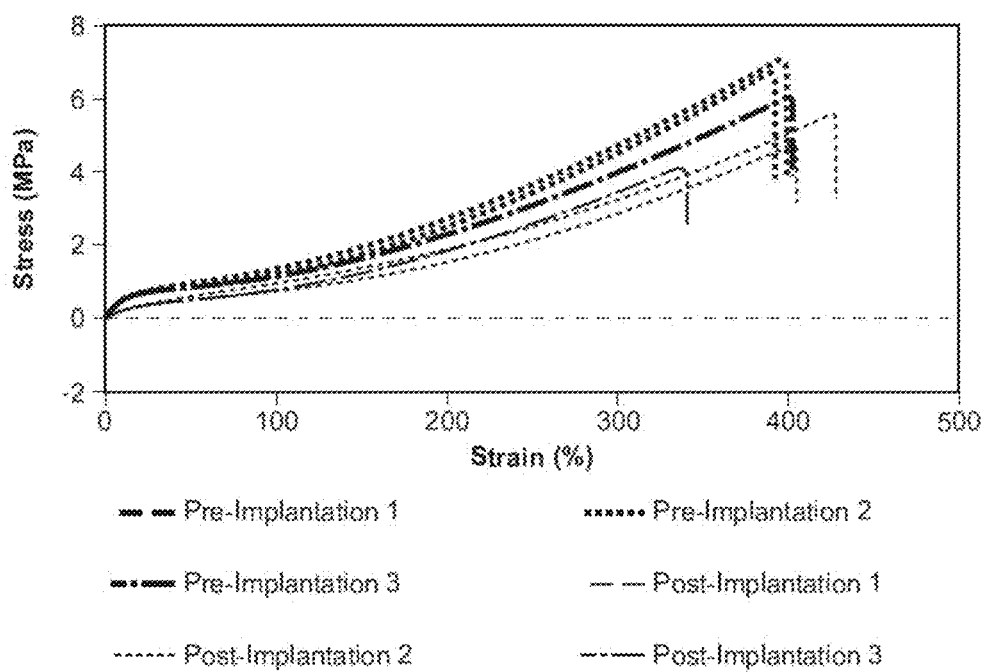
FIG. 7B is a graphic depiction of representative uniaxial mechanical testing loading of pre-implantation and post-implantation electrospun scaffolds according to an embodiment as disclosed herein.
Figures 7C, 8:
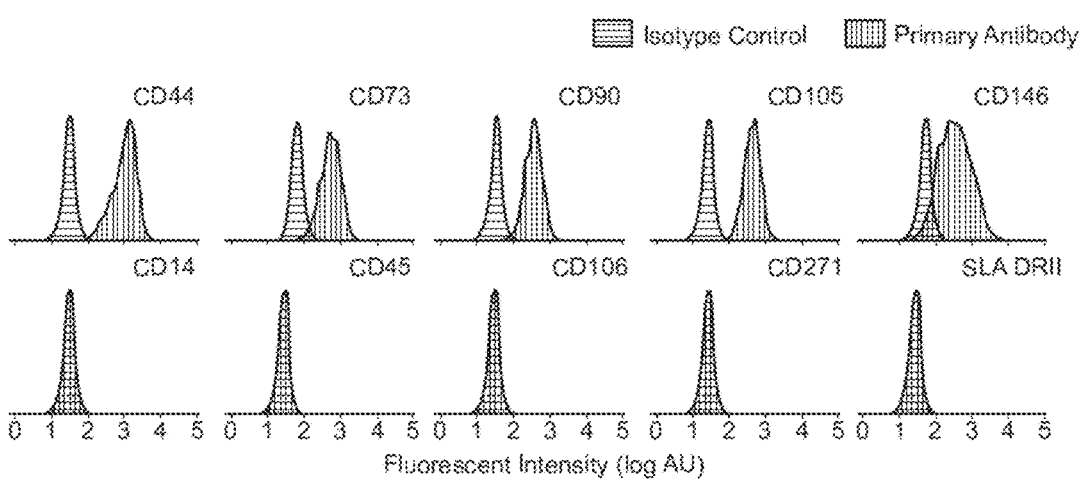
FIG. 7C is a Table directed to the uniaxial mechanical properties of pre- and post-implantations scaffolds prepared according to an embodiment as disclosed herein.
FIG. 8 is a diagrammatic representation of flow cytometry of MSCs isolated and propagated from adipose tissue for up to 5 passages.
Figure 9:
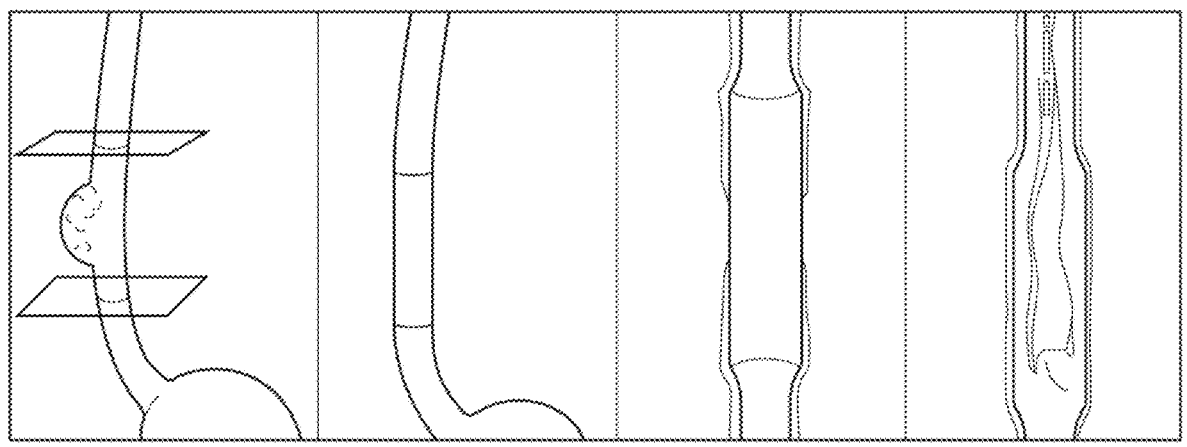
FIG. 9 is an overview of implantation surgery according to an embodiment as disclosed herein.

Tensile testing via uniaxial mechanical loading was performed on three pre-implantation and three post-implantation scaffolds (FIG. 7B), which all showed similar results at in vivo loading values. Consistency between the six samples at in vivo loading shows that the scaffolds have a low degree of variability present after fabrication and in vivo implantation (FIGS. 7B, C). The mean (±SD) tensile strain ranged between 119.5±1.61 mm and 124.5±3.44 mm across the six scaffolds. At failure, the tensile strain for the samples pre-implantation reached 397.38%±5.52% and post-implantation 408.61%±17.64%. Strain values above 400% suggest the reliability of the fabrication process and relative in vivo stability. Tensile stress at failure was 7.25±0.59 MPa and 4.43±0.77 MPa for pre- and post-implantation scaffolds, respectively. Consequently, the Young's modulus was larger in the pre-implantation samples than the post-implantation samples, though both groups were comparable in elasticity at in vivo strains (FIGS. 7B, C). The load at failure followed the same trend as the Young's modulus, with the pre-implantation values being greater than the post-implantation values.

Autologous porcine adipose-derived mesenchymal stem cells (aMSCs) were isolated from 8 pigs following an open adipose biopsy and analyzed for characterization. The 8 Yucatan mini-pigs underwent general anesthesia and chlorhexidine skin preparation prior to a sterile, open adipose tissue biopsy taken from the lateral abdominal wall. A 5 cm incision was performed next to the linea alba with hemostasis achieved using electrocautery. Approximately 30-50 g of adipose tissue was isolated and transferred to a 50 mL conical tube containing alpha Minimal Essential Medium (MEM)/glutamax (Thermo Fisher Scientific, Waltham, MA) and 1% penicillin/streptomycin (Thermo Fisher Scientific).

20-60 g of abdominal adipose tissue was surgically excised from each anesthetized Yucatan mini pig (50-60 kg body weight). The tissue samples were washed 3 times in alpha Minimal Essential Medium (MEM)/glutamax (Thermo Fisher Scientific) and 1% penicillin/streptomycin (Thermo Fisher Scientific). The washed tissue was trimmed to remove lymph nodes and blood vessels and minced into pieces smaller than 5 mm. The tissue pieces were dissociated in digestion buffer (300 IU/mL collagenase type II, 0.1% bovine serum albumin (7.5%, fraction V), 1% penicillin/streptomycin, alpha MEM/glutamax) for 55 minutes at 37° C., 5% $CO_2$. After quenching in complete growth medium (StemXVivo, R&D Systems, Minneapolis, MN) and 1% penicillin/streptomycin), the cells were centrifuged for 15 minutes at 1500 rpm. The cell pellet was re-suspended in 5 mL of growth medium and filtered through a 70 µm filter. The cell filtrate was centrifuged for 5 minutes at 1500 rpm. The cell pellet was re-suspended in 5 mL of growth medium and cells were plated according to tissue weight (3 g of adipose tissue isolate per T75 flask containing 20 mL growth medium).

Cells were washed twice in PBS without calcium or magnesium (Thermo Fisher Scientific) and dissociated using TrypLe (Thermo Fisher Scientific). The dissociation was quenched with growth medium and the cells were centrifuged at 1000 rpm for 5 minutes. The cell pellet was re-suspended in 1% bovine serum albumin diluted with PBS. Aliquots of 1 million cells were incubated in antibody at 4° C. for 30 minutes in the dark (Supplemental Table 1). The labeled cells were washed 3 times in buffer and secondary antibodies (Life Technologies, Carlsbad, CA) were applied as necessary at 4° C. for 30 minutes in the dark. After a further 3 washes, the cell suspensions were placed into a 96 well plate for flow cytometry (Guava easyCyte HT, EMD Millipore, Billerica, MA). Events representative of live cells were gated on forward and side scatter values, based upon measurements of viability (ViaCount, EMD Millipore). Cell type analysis was performed using fluorescent events compensated against unstained and isotype control antibody stained samples. Acquired data was exported and analyzed using standalone software (FlowJo version 10, FlowJo, LLC, Ashland, OR).

To assess colony formation, adipose-derived cells were isolated as described, triturated to a single cell suspension and diluted to 10 cells/mL of growth medium. 100 µL of the cell suspension was added to each well of a 96 well plate (Corning, Inc., Corning, NY) and visually inspected for cell number the following day. After 5-7 days, colonies of cells became visible and medium was changed every 3 days until the colonies contained at least 50 cells. Wells were counted for the presence of colonies and expressed as a percentage of total wells analyzed.

Pluripotency of isolated adipose-derived cells were determined by their ability to undergo adipogenesis and osteogenesis by chemical induction. Cells were plated in 6-well tissue-culture plates, cultured in complete growth medium, and allowed to grow to 60% or 100% confluency for adipogenic and osteogenic differentiation, respectively. Upon reaching confluence, medium was changed to either adipogenic or osteogenic differentiation medium (CCM007, R&D Systems, Minneapolis, MN). Medium was changed every 2 days until 14 days in culture. Cells cultured in adipogenic differentiation medium were stained with Oil Red O (American MasterTech, Lodi, CA) to identify lipids and cells cultured in osteogenic medium were stained with Alizarin Red (EMD Millipore) for calcium deposition.

Concentrations of glucose and lactate were measured in conditioned medium from bioreactors at the time of seeding and 2, 5 and 7 days post-seeding (iSTAT, Abbott, Princeton, NJ).

Cell supernatants were analyzed for the production of porcine cytokines and growth factors either by multiplex assay on the Luminex 200 platform or by ELISA at the University of Minnesota Cytokine Reference Laboratory using commercially available kits and performed according to manufacturers' directions. A 13-plex porcine-specific bead-set panel (EMD Millipore) was used to determine levels of porcine VEGF, GM-CSF, IL-1RA, IL-6 and IL-8. Values were interpolated from standard curves generated on each plate using BioPlex software (BioRad, Hercules, CA) for the Luminex platform, or Microplate Manager software for ELISA plates read on a BioRad 550 plate reader. All samples were assayed in duplicate.

Cells were rinsed in PBS and fixed with 10% formalin for 15 minutes at room temperature. The cells were gently rinsed 3 times in PBS containing 0.1% Triton X-100 (PBS-T) and incubated for 1 hour at room temperature in 10% normal goat serum (Vector) diluted in PBS-T. The rabbit anti-nestin antibody (Biolegend, 1:100) was diluted in 10% normal goat serum and PBS-T and incubated overnight at 4° C. The cells were rinsed twice in PBS-T and incubated in fluorescent goat anti-rabbit antibody (Alexa Fluor 594, Thermo Fisher Scientific) at room temperature for 1 hour. The cells were rinsed twice and counterstained with 4',6-diamidino-2-phenylindole (DAPI).

After 48 hours at 37° C., the cells were washed twice in phosphate buffered saline containing calcium and magnesium (Thermo Fisher Scientific) and replaced with fresh growth medium. Thereafter, culture medium was replaced every 2 days until the flasks were 70%-80% confluent. At passaging, the cells were dissociated (TrypLe, Thermo Fisher Scientific), counted (Countess, Thermo Fisher Scientific) and replated at 200,000 cells per T175 flask. The cells were passaged twice prior to seeding of scaffolds.

Each 11 cm long scaffold was placed in a bioreactor and seeded with 32 million cells (viability >70%, trypan blue dye exclusion, Countess, Thermo Fisher Scientific) in growth medium supplemented with 0.1875% sodium bicarbonate (Thermo Fisher Scientific), MEM eagle (Lonza) and 1.19 mg/mL bovine collagen (Organogenesis) in 0.01M hydrochloric acid. The cells were incubated for 5 minutes at 37° C., 5% $CO_2$ before 200 mL of growth medium was slowly added to the bioreactor. The bioreactor was incubated for 7-8 days prior to scaffold implantation. Culture media was changed every 2 days and taken for various assays described below.

Figure 6:
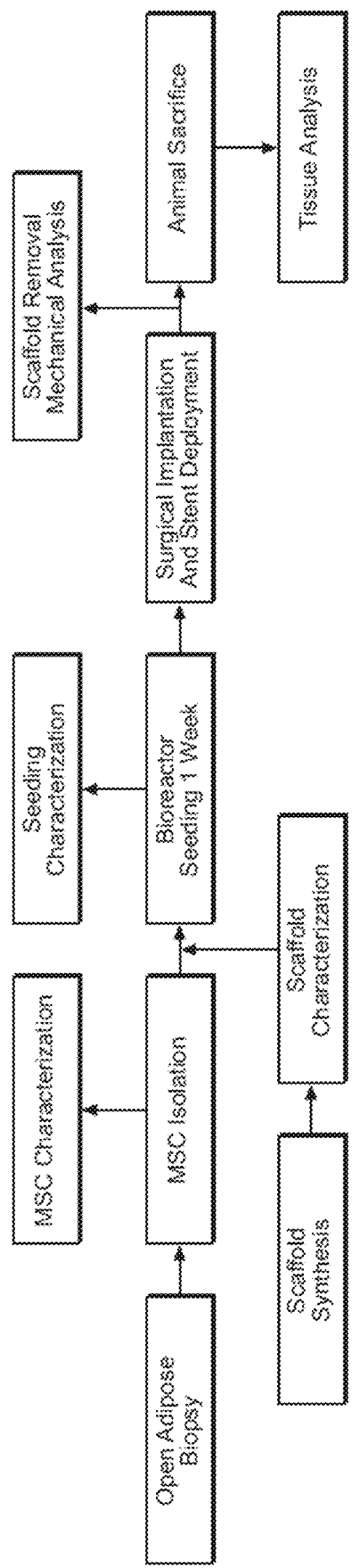
FIG. 6 is an overall study flow for an embodiment of the process as disclosed herein including generation of a cellularized scaffold and subsequent implantation

The porcine aMSCs were seeded onto a previously characterized scaffold and subsequently incubated in a bioreactor. Seeded scaffolds were then implanted following esophagus resection in Yucatan mini-pigs until scaffold removal at 3 weeks (FIG. 6) and reproducibly stained positive for known MSC markers using anti-porcine CD44, CD73, CD90, CD105, and CD146, antibodies and were negative for CD14, CD45, CD106, CD271, and SLA Class II DR. Greater than 95% of the cultured cells stained positive for nestin and aSMA, indicating stem cell characteristics are maintained in culture. Pluripotency was determined by chemically inducing the porcine MSC isolates to undergo adipogenesis and osteogenesis, respectively. These aMSCs were routinely expanded and characterized from passage 1 to 5, and showed consistent phenotypic and functional characteristics.

Porcine aMSCs grown from passage 2 were seeded onto a polymeric scaffold and incubated in a bioreactor for 7 days (+/−1 day) at 37° C. A number of cytokines and growth factors were measured using enzyme-linked immunosorbent assay (ELISA) to determine if the seeded aMSCs cultured on the scaffold secrete factors that may assist in angiogenesis and immunomodulation. Cell secretion of vascular endothelial growth factor (VEGF), granulocyte-macrophage colony-stimulating factor (GM-CSF), interleukin (IL)-6, IL-8, and IL-1RA was detected in conditioned medium at levels significantly above medium alone (FIG. 4A). However, additional cytokines, TNF-α, IL-1α, IL-1β, INF-γ, IL-10, IL-12, IL-18, platelet-derived growth factor (PDGF), and regulated on activation, normal T expressed and secreted (RANTES), were measured but not detected.

Punch biopsies of sections of the seeded graft were taken at the end of the incubation time at 7 days, to assess cell health and penetration into the scaffold. Cellular health was assessed by immunofluorescence staining using calcein (live cells) and ethidium bromide (dead cells). Cellular penetration of the scaffold was assessed using ethidium bromide for cell identification. The populations of live cells attached to the scaffold are indicated by the predominance of calcein staining of the biopsy samples. On cross sections of the scaffold biopsies the majority of cellular attachment was present at the surface of the scaffold. While there was some evidence of cellular proliferation and ingrowth within the scaffold. Metabolic activity of the implant graft during bioreactor incubation was measured every 48 hours for glucose uptake and lactate production. Measurements of conditioned medium consistently indicated decreased glucose and increased lactate levels over time, both indicators of continued metabolic cell growth. In addition, cell expansion over 7 days in the bioreactor was quantified by total DNA content which increase several fold over the course of bioreactor cell seeding. Further characterization of cell phenotype on the scaffold following 7 days incubation shows cells continue to express alpha smooth muscle actin (aSMA) and nestin.

After endotracheal intubation and induction of general anesthesia, animals were placed in a left lateral decubitus position. Hair was clipped and Chlorhexidine or povidone iodine was used for skin preparation and the animal was sterilely draped. A standard right thoracotomy at the level of the $4^{th}$ intercostal space on each animal was performed and the thoracic cavity was entered. Single lung ventilation was achieved through the use of a double lumen endotracheal tube. A 4-4.5 cm segment of the esophagus, located in the mid thoracic region (posterior to the right lung hilum, was circumferentially mobilized and resected to generate a 6 cm defect (tissue retraction proximally and distally). The seeded scaffold (6 cm length) was then implanted using polydioxanone (PDS, Ethicon Inc., Somerville, NJ) absorbable sutures with anastomosis to the proximal and distal esophagus. After the implantation, a commercially available esophageal stent (WallFlex M00516740, Boston Scientific) was inserted under direct endoscopic guidance (Storz Video Gastroscope Silver Scope 9.3 MM×110 CM, Tuttlingen, Germany). Stent deployment was performed under endoscopic and surgical visualization. The esophageal stent was fixed in place to the normal esophageal tissue using absorbable suture, at both the proximal and distal stent flares.

Postoperatively the animals were adjunct supported by gastrostomy feeding and maintained on a liquid diet through a feeding tube for 2 weeks, a mashed diet for a period of 2 more weeks, and then allowed to eat an oral diet of solid food after for the continuation of the study.

At approximately 21 days following the implantation, the scaffolds were retrieved endoscopically and aMSC impregnated platelet rich plasma (PRP) gel was applied to improve the healing process of the newly formed esophageal conduit. After PRP application, a new fully covered esophageal stent (WallFlex™, 12 cm long×23 mm outer diameter, Boston Scientific Corporation) was placed across the implant zone to prevent stricture formation and to maintain anatomy during regeneration. Every two weeks the animals underwent sedation and assessment of the esophageal anastomosis and esophageal stent exchange to allow direct visualization and progression of esophageal regeneration. Follow-up observations were conducted endoscopically (Storz Video Gastroscope Silver Scope 9.3 MM×110 CM, Tuttlingen, Germany).

Figure 10:
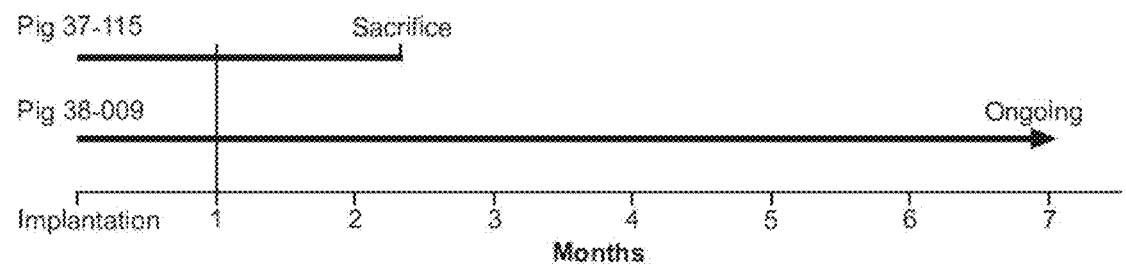
FIG. 10 is a representation of a timeline according to an embodiment of the process as disclosed herein.

Regeneration progression was also assessed by endoscopic inspection. Following scaffold removal. the implant zone was visualized endoscopically at approximately 3-4 week intervals; 2 representative animals are shown (FIGS. 10 and 11). At 3-4 weeks post-implantation, regeneration of the mucosal layer was only partially complete. However, the process of esophageal healing continued with time, indicated by the proximal and distal ends of the mucosal layers forming an initial ridge before fusion of the 2 layers and complete mucosal regeneration. The early reconstitution of the esophageal continuity and integrity and the subsequent growth of the submucosa from the two opposite edges of the resection have been consistent across all eight animals; 2 animals have been maintained to 8 and 9 months post-surgery and have been without esophageal stent respectively for 2 and 3 months without evidence of stricture or stenosis and have had durable oral intake, with noteworthy weight gain.

Figure 13A:
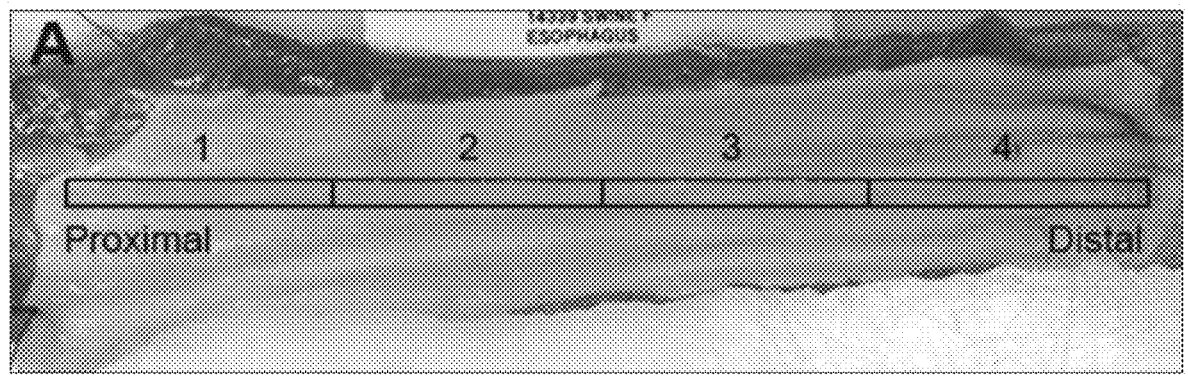
FIG. 13 A is a photograph of tissues from a representative test animal esophagus at 2.5 months post implantation including the surgical site and adjacent distal and proximal tissues excised for histological analysis.
FIG. 13B is a photograph of a magnified cross-sectional sample of mucosa tissue taken from proximal section 1 of FIG. 13A.
FIG. 13C is a photograph of a magnified cross-sectional sample of mucosa tissue taken from proximal section 2 of FIG. 13A.
FIG. 13D is a photograph of a magnified cross-sectional sample of submucosa tissue taken from proximal section 1 of FIG. 13A.
FIG. 13E is a photograph of a magnified cross-sectional sample of submucosa tissue taken from proximal section 2 of FIG. 13A.
FIG. 13F is a photograph of a magnified cross-sectional sample of mucosa tissue taken from distal section 3 of FIG. 13A.
FIG. 13G is a photograph of a magnified cross-sectional sample of mucosa tissue taken from distal section 4 of FIG. 13A.
FIG. 13H is a photograph of a magnified cross-sectional sample of mucosa tissue taken from distal section 4 of FIG. 13A.
FIG. 13I is a photograph of a magnified cross-sectional sample of submucosa tissue taken from distal section 4 of FIG. 13A.
Figure 13B:
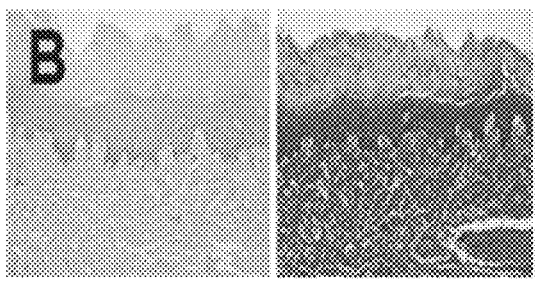
Figure 13C:
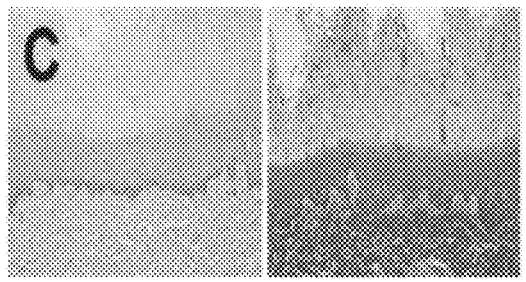
Figure 13:
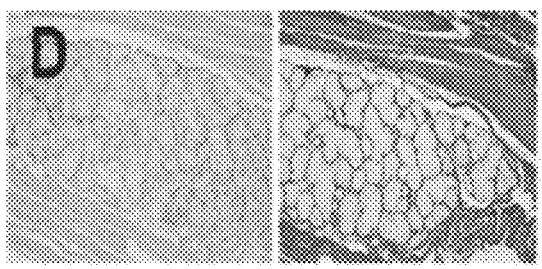
Figure 13:
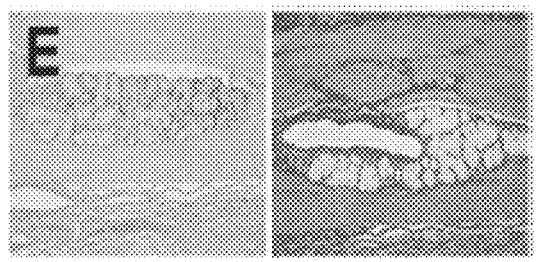
Figure 13:
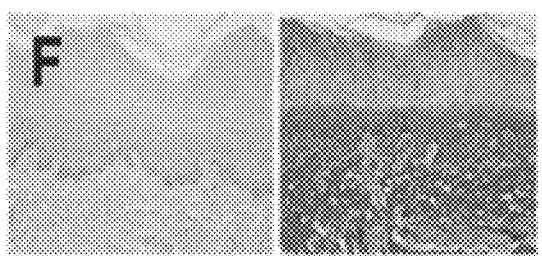
Figure 13:
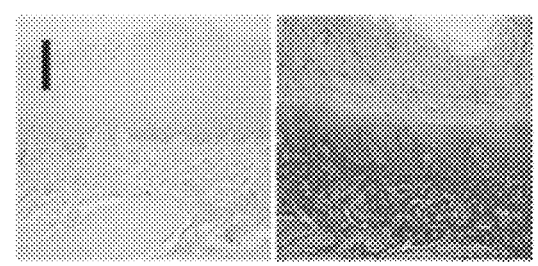
Figure 13:
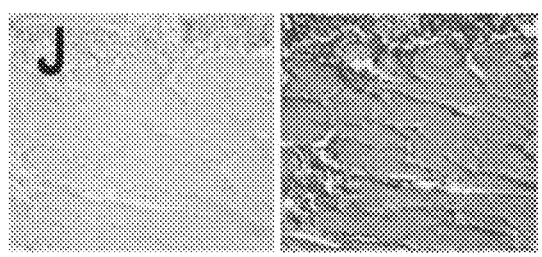
Figure 13:
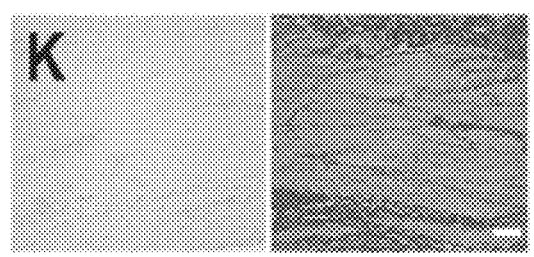
Figure 14F:
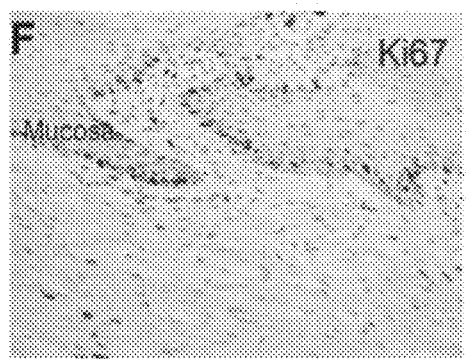
FIG. 14F is a photograph of a cross-sectional sample of esophageal tissue of FIG. 14A used for Ki67 immunoreactivity analysis.
Figure 14G:
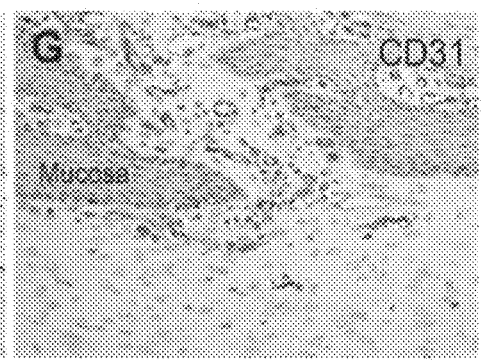
FIG. 14G is a photograph of a cross-sectional sample of esophageal tissue of FIG. 14A used for CD31 immunoreactivity analysis.
Figure 14H:
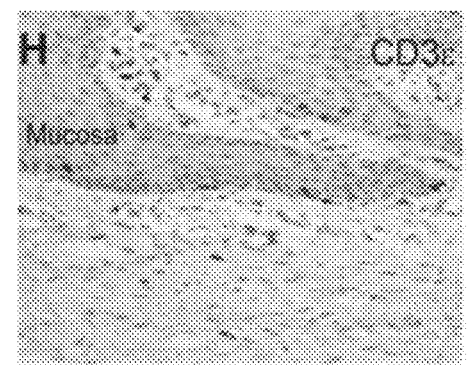
FIG. 14H is a photograph of a cross-sectional sample of esophageal tissue of FIG. 14A used for CD3ε immunoreactivity analysis.
Figure 14I:
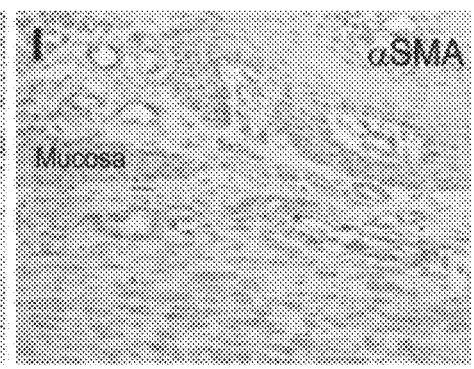
FIG. 14I is a photograph of a cross-sectional sample of esophageal tissue of FIG. 14A used for αSMA immunoreactivity analysis.
Figure 14J:
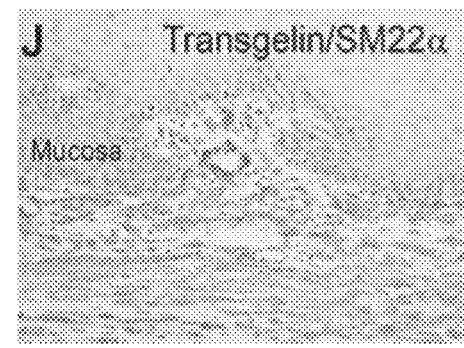
FIG. 14J is a photograph of a cross-sectional sample of esophageal tissue of FIG. 14A used for Transgelin/SMA22α immunoreactivity analysis.
Figure 14K:
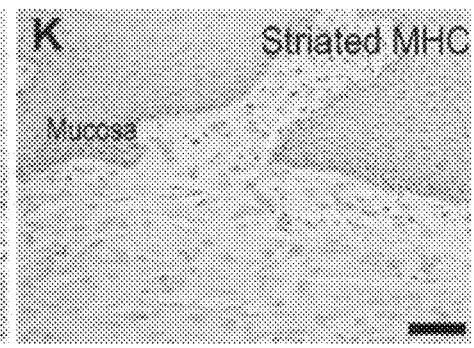
FIG. 14K is a photograph of a cross-sectional sample of esophageal tissue of FIG. 14A.

In order to ascertain histological similarities of the morphologies of regenerated and native esophageal tissue. Samples of tissue were excised from a representative pig esophagus at 2.5 months post-implantation, and include both the site of surgery and adjacent distal and proximal tissues for histology. (FIG. 13A, dotted box indicates the histological analysis specimens). Representative images of hematoxylin and eosin (FIGS. 13B and D) and Masson's trichrome (FIGS. 13C and E) stained tissue sections show histologically intact multi-layered esophageal epithelia and submucosa and normal inner muscular layer morphology.

Representative immunohistochemical analysis from the regenerated region is depicted in FIG. 14 which depicted histological analysis of tissue from pig esophagus at 2.5 months post implantation of a cellularized scaffold as described herein. FIG. 14A depicts a macroscopic image of excised esophagus (proximal suture to the left). Samples of tissue were excised to include the site of surgery, monitored by endoscopy, with adjacent distal and proximal tissues for histology (dotted box). (FIGS. 14 B-E) Representative images of hematoxylin and eosin (FIGS. 14 B, D) and Masson's trichrome (FIGS. 14 C, E) stained tissue sections. Scale bars: A=6 cm, B, C, D and E=200 µm. Representative immunohistochemical analysis demonstrates immunoreactivity for Ki67 (FIG. 14F) suggesting continued proliferation of mucosal and submucosal cells, CD31 (FIG. 14G), CD3e (FIG. 14H), aSMA (FIG. 14I), transgelin/SM22a (FIG. 14J) and a relative absence of striated myosin heavy chain (K) in tissue at the site of surgery. Scale bars: F-K=200 µm. demonstrates immunoreactivity for Ki67 (FIG. 14F) at 2.5 months suggests continued proliferation of mucosal and submucosal cells, CD31 (FIG. 14G), CD3e (FIG. 7H), aSMA (FIG. 14I), transgelin/SM22a (FIG. 14J) and a relative absence of striated myosin heavy chain (FIG. 14K) in tissue at the site of surgery. The predominance of aSMA, SM22a, and relative absence of myosin heavy chain suggest that smooth muscle proliferation precedes skeletal muscle growth.

The synthetic matrix seeded with autologously derived mesenchymal cells (aMSCs) resulted in full longitudinal regeneration of the resected esophagus with minimal mucosal ulcerations or perforations (Table 1). All animal experienced a full 100% of longitudinal regeneration from 2-9 weeks after graft removal with 1 out of 6 animals experiencing both mucosal ulceration or perforation. No animals experienced leaks over the course of the study.

TABLE I

| Pig No | Time (status) | Stent | Scaffold length (cm) | Longitudinal regeneration (%) | Mucosal ulceration | Contained perforation | Leak |
|---|---|---|---|---|---|---|---|
| 1 | 2 weeks (euthanized) | No | 4.5 | 100 | No | No | |
| 2 | 2 weeks (euthanized) | No | 4.5 | 100 | No | No | |
| 3 | 6 weeks (euthanized) | Yes | 6 | 100 | No | No | |
| 4 | 7 weeks (euthanized) | Yes | 6 | 100 | No | No | |
| 5 | 9 weeks (euthanized) | Yes | 6 | 100 | No | Yes | |
| 6 | 9 weeks (euthanized) | Yes | 6 | 100 | Yes | No | |
| 7 | 7 months (alive) | Yes | 6 | | | | |
| 8 | 7 months (alive) | Yes | 6 | | | | |

Example III—Other Gastrointestinal Implant

The process as outlined in Examples I and II is implemented replacing gastrointestinal regions localized to the rectum. Results are similar to the results outlined previously.

Having thus described several embodiments with respect to aspects of the inventions, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method, comprising the steps of:
resecting a portion of a tubular organ in a subject, the resecting step producing a resected organ portion, the resected organ portion having at least one resection edge having tissue and remaining in the subject at a resection site;
implanting a synthetic polymeric scaffold at the resection site to form an implantation site, the synthetic polymeric scaffold including a body section having an outer polymeric surface, wherein the outer polymeric surface includes spun polymeric fibers, and a cellularized sheath layer overlying at least a portion of the outer polymeric surface of the body section;
maintaining the synthetic polymeric scaffold at the implantation site formed at the resection site for a period of time sufficient to achieve guided tissue growth along the synthetic polymeric scaffold, the guided tissue growth derived from and in contact with the tissue at the at least one resection edge present in the resected organ portion remaining in the subject at the resection site; and
after achieving the guided tissue growth, intrascopically removing the synthetic polymeric scaffold from the implantation site, the removing step occurring in a manner such that the guided tissue growth remains in contact with the resected organ portion of the tubular organ remaining in the subject,
wherein the guided tissue growth achieved comprises multilayered muscle tissue and epithelia configured as a lumen.

2. The method of claim 1 comprising the steps of:
imparting cellular material onto the outer polymeric surface of the synthetic polymeric scaffold; and
allowing the cellular material to grow to form the cellularized sheath layer, the imparting and allowing steps occurring prior to the resecting step.

3. The method of claim 2 wherein the synthetic polymeric scaffold is a tubular member.

4. The method of claim 2 wherein the cellularized sheath layer spans and overlies at least a portion of the spun polymeric fibers of the outer polymeric surface.

5. The method of claim 1 wherein the cellularized sheath layer is composed of cellular material, the cellular material including at least one of mesenchymal cells, stem cells, pluripotent cells.

6. The method of claim 1 wherein the tubular organ is a gastrointestinal organ.

7. The method of claim 6 wherein the gastrointestinal organ is an esophagus.

8. The method of claim 1, wherein the synthetic polymeric scaffold comprises: the body section having a first end and a second end opposed to the first end, and
wherein the spun polymeric fibers of the body section have an average fiber diameter between 15 nm and 10 microns, at least a portion of the spun polymeric fibers interlinked to form pores having an average diameter less than 50 microns.

9. The method of claim 8 wherein the spun polymeric fibers are electrospun and are interconnected and form the outer polymeric surface of the body section and the body section further comprises at least one inner layer, the inner layer composed of at least one of a polymeric mesh, a polymeric braided support material, a solid polymeric member, or an electrospun layer, wherein the outer polymeric surface is in overlying contact with the inner layer.

10. The method of claim 9 wherein the electrospun polymeric fibers have an average fiber diameter of 3 to 10 micrometers and is composed of at least one of one of the following polymeric materials: polyvinylidene fluoride, syndiotactic polystyrene, copolymer of vinylidene fluoride and hexafluoropropylene, polyvinyl alcohol, polyvinyl acetate, poly(acrylonitrile), copolymers of polyacrylonitrile and acrylic acid, copolymers of polyacrylonitrile and methacrylates, polystyrene, poly(vinyl chloride), copolymers of poly(vinyl chloride), poly(methyl methacrylate), copolymers of poly(methyl methacrylate), polyethylene terephthalate, or polyurethane.

11. The method of claim 9 wherein at least one layer of the synthetic polymeric scaffold is a polymeric material containing polyethylene terephthalate, polyurethane, blends of polyethylene terephthalate and polyurethane.

12. The method of claim 9 wherein the polymeric braided support material of the synthetic polymeric scaffold is composed of at least one of polyethylene terephtalate, polyurethane, and mixtures thereof.

13. The method of claim 9 wherein the cellularized sheath layer of the synthetic polymeric scaffold is composed of cellular material, the cellular material composed of mesenchymal cells and stem cells present in a defined layer the defined layer being between 1 and 100 cells thick.

14. The method of claim 13 wherein the cellularized sheath layer overlays the electrospun fibers such that the cellular material, spans the pores defined in the outer surface.

15. The method of claim 8 wherein the synthetic polymeric scaffold further comprises at least one hole, indent, protrusion, or a combination thereof defined proximate to at least one of the first or second ends that is adapted to assist in the retrieval of the synthetic polymeric scaffold from the subject after tissue regeneration has occurred around the scaffold at the implantation site in the subject.

16. A method, comprising:

resecting a portion of a tubular organ in a subject, the resection step producing a resected tubular organ portion at a resection site, the resected tubular organ portion having a resection edge remaining in the subject;

implanting a synthetic polymeric scaffold at the resection site, the synthetic polymeric scaffold having an outer polymeric surface and including a first end and a second end opposed to the first end, the outer polymeric surface positioned between the first end and the second end and a cellularized sheath layer overlying at least a portion of the outer polymeric surface, wherein at least a portion to the cellularized sheath layer is proximate to the resection edge of the resected tubular organ portion:

maintaining contact between the synthetic polymeric scaffold and the resection edge for a period of time sufficient to achieve guided tissue growth along the synthetic polymeric scaffold, wherein the guided tissue growth achieved comprises multilayered muscle tissue and epithelia configured as a lumen; and intrascopically removing the synthetic polymeric scaffold after the guided tissue growth is achieved.

17. The method of claim 16 further comprising:

imparting cellular material onto the outer polymeric surface of the synthetic polymeric scaffold; and allowing the cellular material to grow into the cellularized sheath layer, the imparting and allowing steps occurring prior to the resecting step.

18. The method of claim 17 wherein the synthetic polymeric scaffold is configured as a tubular member where the outer polymeric surface includes electrospun polymeric fibers and wherein cellularized sheath layer spans at least a portion outwardly positioned electrospun polymeric fibers.

19. The method of claim 18 wherein the cellular material includes one of mesenchymal cells, stem cells, pluripotent cells, the cellular material derived from the subject.

20. The method of claim 17, further comprising monitoring tissue regeneration endoscopically.

21. The method of claim 16, wherein the tubular organ is a gastrointestinal organ.

22. The method of claim 21, wherein the gastrointestinal organ is an esophagus.

23. The method of claim 16, wherein the subject is a mammal.

24. The method of claim 23, wherein the mammal is a human.

* * * * *